(12) United States Patent
Yokota et al.

(10) Patent No.: US 8,329,670 B2
(45) Date of Patent: Dec. 11, 2012

(54) SYSTEM FOR DELIVERING NUCLEIC ACIDS FOR SUPPRESSING TARGET GENE EXPRESSION BY UTILIZING ENDOGENOUS CHYLOMICRON

(75) Inventors: Takanori Yokota, Tokyo (JP); Kazutaka Nishina, Tokyo (JP); Hidehiro Mizusawa, Tokyo (JP); Toshinori Unno, Tokyo (JP)

(73) Assignee: National University Corporation Tokyo Medical and Dental University, Tokyo (JP)

( * ) Notice: Subject to any disclaimer, the term of this patent is extended or adjusted under 35 U.S.C. 154(b) by 213 days.

(21) Appl. No.: 12/787,552

(22) Filed: May 26, 2010

(65) Prior Publication Data
US 2010/0234282 A1 Sep. 16, 2010

Related U.S. Application Data

(63) Continuation-in-part of application No. PCT/JP2008/003523, filed on Nov. 28, 2008.

(60) Provisional application No. 60/990,796, filed on Nov. 28, 2007.

(51) Int. Cl.
| | |
|---|---|
| *C07H 21/02* | (2006.01) |
| *C07H 21/04* | (2006.01) |
| *A61K 31/70* | (2006.01) |
| *A61K 48/00* | (2006.01) |
| *C12Q 1/68* | (2006.01) |
| *C12N 5/00* | (2006.01) |

(52) U.S. Cl. .............. 514/44 A; 514/44 R; 435/375; 435/377; 536/23.1; 536/24.1; 536/24.5

(58) Field of Classification Search .................. None
See application file for complete search history.

(56) References Cited

FOREIGN PATENT DOCUMENTS
| | | |
|---|---|---|
| JP | 07-194385 | 8/1995 |
| JP | 07-303487 | 11/1995 |
| JP | 2007-506790 | 3/2007 |

OTHER PUBLICATIONS

Hara et al., "In vivo gene delivery to the liver using reconstituted chylomicron remnants as a novel nonviral vector," Proc. Natl. Acad. Sci., vol. 94, No. 26, pp. 14547-14552, Dec. 1997.
Nishina et al., "Efficient In Vivo Delivery of siRNA to the Liver by Conjugation of α-Tocopherol," The American Society of Gene Therapy, vol. 16, No. 4, pp. 734-740, Apr. 2008.
Okamoto et al., "Attempt for liver-targeted delivery of antisense oligonucleotides by cholesterol modification and oral administration," Hepatology Research, vol. 13, pp. 252-258, 1999.
Wolfrum et al., "Mechanisms and optimization of in vivo delivery of lipophilic siRNAs," Nature Biotechnology, vol. 25, No. 10, pp. 1149-1157, Oct. 2007.
Supplementary European Search Report from EP 08853448.4 dated Oct. 26, 2011.
Wolfrum et al., "Mechanisms and Optimization of in vivo Delivery of Lipophilic siRNAs," Nature Biotechnology, 25(10), pp. 1149-1157, Oct. 2007.

*Primary Examiner* — Sean McGarry
(74) *Attorney, Agent, or Firm* — Kenneth H. Sonnenfeld; Margaret B. Brivanlou; King & Spalding

(57) ABSTRACT

The object of present invention is to provide a system that can deliver in vivo nucleic acids such as an siRNA for suppressing a target gene expression in vivo more safely and efficiently, and to provide an expression-suppressing agent and a pharmaceutical composition utilizing the system. An introduction substance into chylomiclon, particularly nucleic acids to which an alpha-tocopherol is bound for suppressing a target gene expression, can be delivered more safely and efficiently into hepatic cells in vivo by administering the nucleic aids under the condition where the production of chylomicron is induced in the body. Alternatively, alpha-tocopherol-bound nucleic acids are mixed with extracted chylomiclon, and then they are administered. Consequently, a target gene expression is suppressed, thereby a disease caused by an elevated expression of the target gene can be treated more safely and efficiently.

16 Claims, 17 Drawing Sheets
(3 of 17 Drawing Sheet(s) Filed in Color)

Chemical structure of alpha-tocopherol-conjugated siRNA

27/29 mer Toc-siRNA/LP was transduced to Hep 1-6 cell line and cleaved by Dicer, producing 21 mer siRNA Toc-siRNA/LP effect on ApoB mRNA of mouse liver *in vivo*

Effect of feeding before injection of Toc-siRNA/LP.

Tocopherol-conjugated siRNA

Cholesterol-conjugated siRNA

Green: Alexa488-Phalloidin (Cell membrane)  Red: Cy3 (Nucleic acid)  Blue: To-PRO3 (Nucleus)

Histology of the liver tissue after injection of Toc-siRNA/LP

SYSTEM FOR DELIVERING NUCLEIC ACIDS FOR SUPPRESSING TARGET GENE EXPRESSION BY UTILIZING ENDOGENOUS CHYLOMICRON

This application is a Continuation-in-Part of International Application No. PCT/JP2008/003523 filed Nov. 28, 2008 which claims benefit of priority to U.S. Provisional Application Ser. No. 60/990,796 filed Nov. 28, 2007, the entire contents of which are hereby incorporated by reference herein.

TECHNICAL FIELD

The present invention relates to a system for delivering in vivo nucleic acids such as an siRNA for suppressing a target gene expression, and to an expression-suppressing agent and a pharmaceutical composition utilizing the system.

BACKGROUND ART

An siRNA capable of suppressing the expression of a specific gene is widely used as a research tool. An siRNA is also receiving attention for applications to therapeutic agents for a wide variety of diseases including tumors, infectious diseases, and hereditary diseases. The most critical problem in the clinical applications of an siRNA lies in the fact that an siRNA should be delivered specifically and efficiently to a target cell in vivo. For example, a delivery method is known in which an siRNA is delivered in vivo by means of a high-pressure and high-volume intravenous injection of a synthetic siRNA, utilizing a viral vector. This method, however, uses a viral vector, and a restriction is imposed on the clinical applications of such method from the viewpoint of safety and the like. Consequently, various non-viral systems have been developed that can deliver an siRNA in vivo to the liver, tumor, or other tissues.

Examples of recently developed non-viral delivery systems include the ones using: a cholesterol-siRNA complex (non-patent document 1); stable nucleic acid lipid particles (SNALP) (non-patent document 2); interfering nanoparticles (iNOP) (non-patent document 3) and the like. Among these non-viral delivery systems, SNALP has brought about a great improvement in that the use of SNALP for injecting a clinically appropriate amount of siRNAs has enabled the knockdown of a target mRNA in the liver. However, a therapeutic amount (2.5 mg/kg) of SNALP caused a significant damage to the liver in a crab-eating monkey, whose transaminase level (ALT and AST) exceeded 1000 U/L 48 hours after the administration. Further, a serious disadvantage of SNALP and iNOP is that these delivery systems can only passively transfer an siRNA complex to the liver by utilizing lipophilic nature of the particles that could contribute to the toxicity.

Recently, new types of non-viral delivery systems have been reported, including an siRNA vector (RVG-9R) that can transfer an siRNA via a receptor (non-patent document 4) and "Dynamic PolyConjugate™" (Mirus) (non-patent document 5). The above-mentioned RVG-9R is a short peptide derived from a glycoprotein of rabies virus, added with 9 arginine residues. By utilizing this RVG-9R, an siRNA can be transferred to a nerve cell via an acetylcholine receptor. Meanwhile, the Dynamic PolyConjugate contains a membrane-active form of polymer to which an N-acetylgalactosamine (NAG) is bound, as a ligand targeting a hepatic cell. While the use of these receptor-mediated delivery systems such as RVG-9R and Dynamic PolyConjugate can improve efficiency and specificity of an in vivo siRNA delivery to a target cell, artificially synthesized vector molecules used in these systems still possess hazardous nature that could cause serious side-effects particularly when the dose is increased.

Most recently, a delivery method has been reported, which comprises extracting endogenous lipoprotein, allowing LDL and HDL ex vivo to take in an siRNA to which a cholesterol molecule in the lipoprotein is bound, and introducing the siRNA to the liver via a lipoprotein receptor (non-patent document 6). This complex is taken in by the liver 5 to 8 times more effectively as compared to a free cholesterol-siRNA. However, the complex is effective only to the extent that it can suppress the target gene in the liver by about 55% with a 13 mg/kg intravenous siRNA administration, which is far from sufficient.

Under these circumstances, there have been demands for an siRNA delivery system that can efficiently and specifically deliver an siRNA in vivo and that has a lower risk of causing side-effects.

[Non-Patent Document 1]
Nature 432:173-178, 2004
[Non-Patent Document 2]
Nature 441:111-114, 2006
[Non-Patent Document 3]
ACS Chem. Biol. 2:237-241, 2007
[Non-Patent Document 4]
Nature 448:39-43, 2007
[Non-Patent Document 5]
Proc Natl Acad Sci USA. 104:12982-12987, 2007
[Non-Patent Document 6]
Nature Biotechnology 25:1149-1157, 2007

DISCLOSURE OF THE INVENTION

Technical Problem

The object of the present invention is to provide a system that can in vivo deliver nucleic acids such as an siRNA for suppressing a target gene expression in vivo more safely and efficiently, and to provide an expression-suppressing agent and a pharmaceutical composition utilizing the system.

Technical Solution

The present inventors administered a vitamin E-bound siRNA under the condition where the production of endogenous chylomicron is induced in vivo, and successfully delivered the siRNA in vivo more safely and efficiently. Consequently, the present inventors discovered that a target-gene expression can be suppressed very efficiently, and thus completed the present invention.

More specifically, the present invention relates to an agent for suppressing a target gene expression, comprising nucleic acids for suppressing the target gene expression, wherein an introduction substance into chylomicron or chylomicron remnant is bound to the nucleic acids, and wherein the agent is administered to a vertebrate under a condition in which a production of endogenous chylomicron is induced in the vertebrate (1); the agent according to (1), wherein the condition is a condition of within 12 hours after a lipid is administered to the vertebrate (2); the agent according to (2), wherein the lipid is administered in a form of an oral intake (3); the agent according to (1), wherein LPL inhibitor is administered to a vertebrate before a production of endogenous chylomicron is induced in the vertebrate (4); The agent according to (1), wherein LPL and/or heparin is administered to a vertebrate before nucleic acids are administered to the vertebrate. (5); the agent according to (1), wherein the vertebrate is allowed to be in a state of starvation prior to a lipid administration. (6);

the agent according to (1), wherein the nucleic acids to which an introduction substance into chylomicron is bound are administered to a vertebrate, with the nucleic acids being mixed with concentrated chylomicron obtained from a vertebrate (7); the agent according to (1), wherein the substance is a lipophilic vitamin or cholesterol (8); the agent according to (8), wherein the lipophilic vitamin is vitamin E (9); the agent according to (1), wherein the nucleic acids are one or more kinds of nucleic acids selected from the group consisting of siRNA, shRNA, antisense oligonucleotide, antagomir, nucleic-acid aptamer, ribozyme, and decoy (10); the agent according to (10), wherein the nucleic acids are siRNA (11); the agent according to (1), wherein the nucleic acids are RNA subjected to an anti-RNase treatment (12); and the agent according to (12), wherein the anti-RNase treatment is 2'-O-methylation treatment and/or thiophosphorylation treatment (13).

The present invention also relates to a pharmaceutical composition comprising the agent according to (1) as an active ingredient (14).

The present invention further relates to a method for delivering in vivo nucleic acids for suppressing a target gene expression, comprising administering the nucleic acids to a vertebrate under a condition in which a production of endogenous chylomicron or chylomicron remnant is induced in the vertebrate, wherein an introduction substance into chylomicron is bound to the nucleic acids (15).

The present invention still further relates to a method for treating a disease that is ameliorated by suppressing a target gene expression, comprising administering nucleic acids for suppressing the target gene expression to a vertebrate under a condition in which a production of endogenous chylomicron or chylomicron remnant is induced in the vertebrate, wherein an introduction substance into chylomicron is bound to the nucleic acids (16); the method according to (15) or (16), wherein the condition is a condition of within 12 hours after a lipid is administered to a vertebrate (17); the method according to (17), wherein the lipid is administered in a form of an oral intake (18); the method according to (15) or (16), comprising administering LPL inhibitor to a vertebrate before a production of endogenous chylomicron is induced in the vertebrate. (19); The method according to (15) or (16), comprising administering LPL and/or heparin to a vertebrate before nucleic acids are administered to the vertebrate. (20); the method according to (15) or (16), comprising allowing the vertebrate to be in a state of starvation prior to a lipid administration (21); the method according to (15) or (16), comprising administering to a vertebrate the nucleic acids to which an introduction substance into chylomicron is bound, with the nucleic acids being mixed with concentrated chylomicron obtained from a vertebrate (22); The method according to (22), comprising administering LPL and/or heparin to a vertebrate before nucleic acids are administered to the vertebrate. (23); the method according to (15) or (16), wherein the substance is a lipophilic vitamin or cholesterol (24); the method according to (24), wherein the lipophilic vitamin is vitamin E (25); the method according to (15) or (16), wherein the nucleic acids are one or more kinds of nucleic acids selected from the group consisting of siRNA, shRNA, antisense oligonucleotide, antagomir, nucleic-acid aptamer, ribozyme, and decoy (26); the method according to (26), wherein the nucleic acids are siRNA (27); and the method according to (15) or (16), wherein the nucleic acids are RNA subjected to an anti-RNase treatment (28).

BRIEF DESCRIPTION OF DRAWINGS

The file of this patent contains at least one drawing executed in color. Copies of this patent with color drawing(s) will be provided by the Patent and Trademark Office upon request and payment of the necessary fee.

A: This figure shows the Toc-siRNA sequence targeted to the mouse apoB mRNA and the chemical modification of the sequence.
B. This figure shows the stability of the modified siRNA in a serum.
C: This figure shows the in vitro expression-suppressing efficiency of the modified siRNA.

Figure 4:
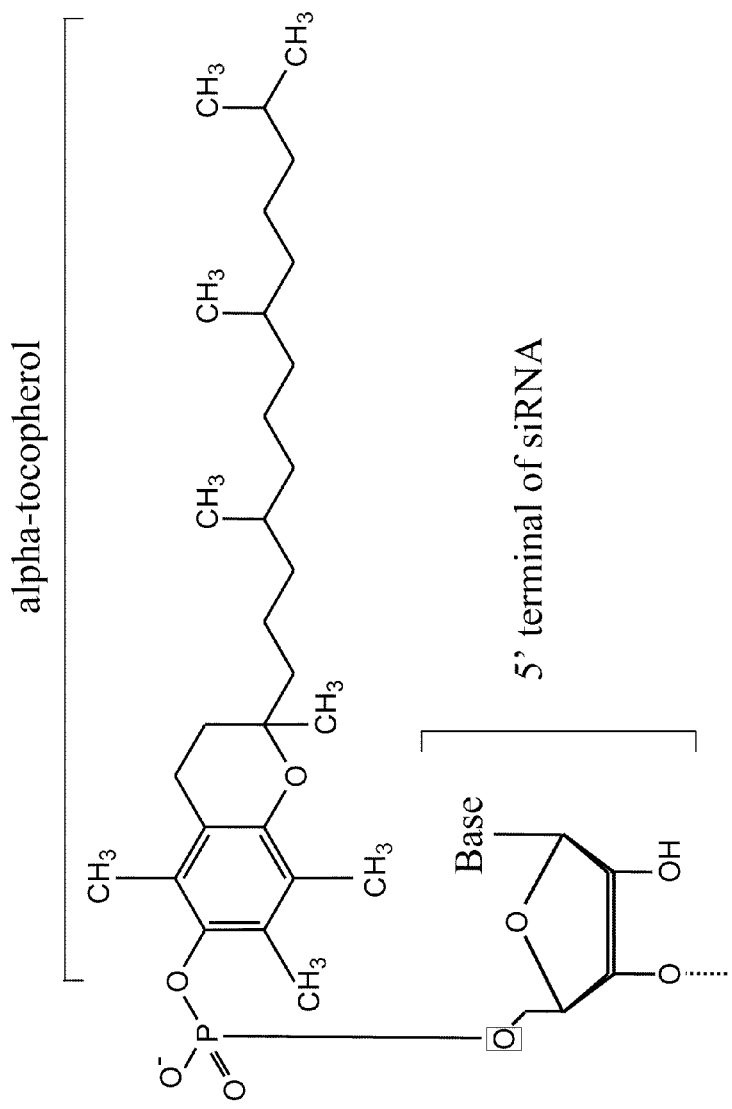

FIG. 4 This figure shows the chemical structure of an alpha-tocopherol (vitamin E)-bound siRNA.

Figure 5:
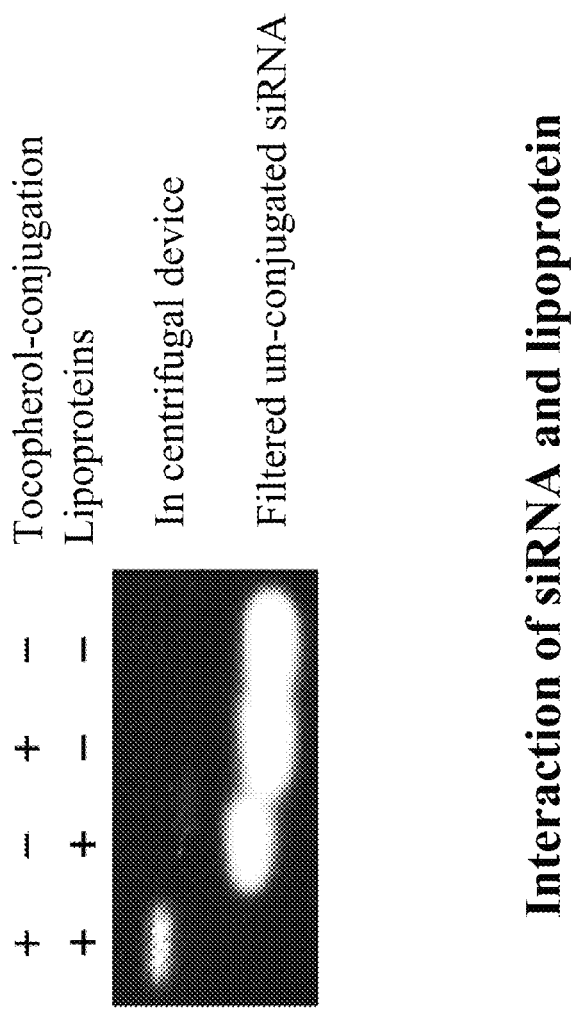

FIG. 5 This figure shows the interaction of an siRNA with a lipoprotein.

Figure 6:
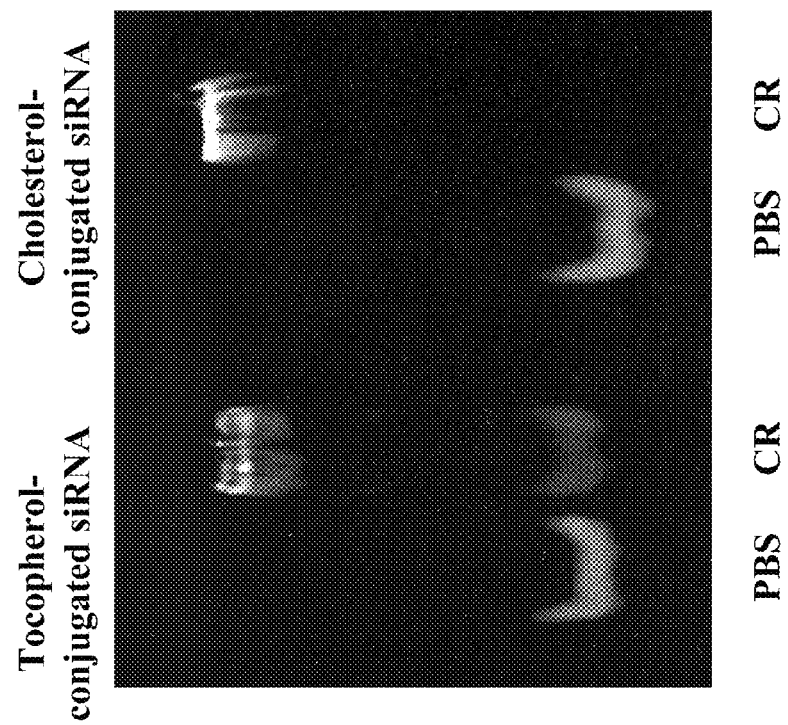

FIG. 6 This figure shows the interaction of a Toc-siRNA or Cho-siRNA and a lipoprotein (the results of an acrylamide gel electrophoresis).

Figure 7:
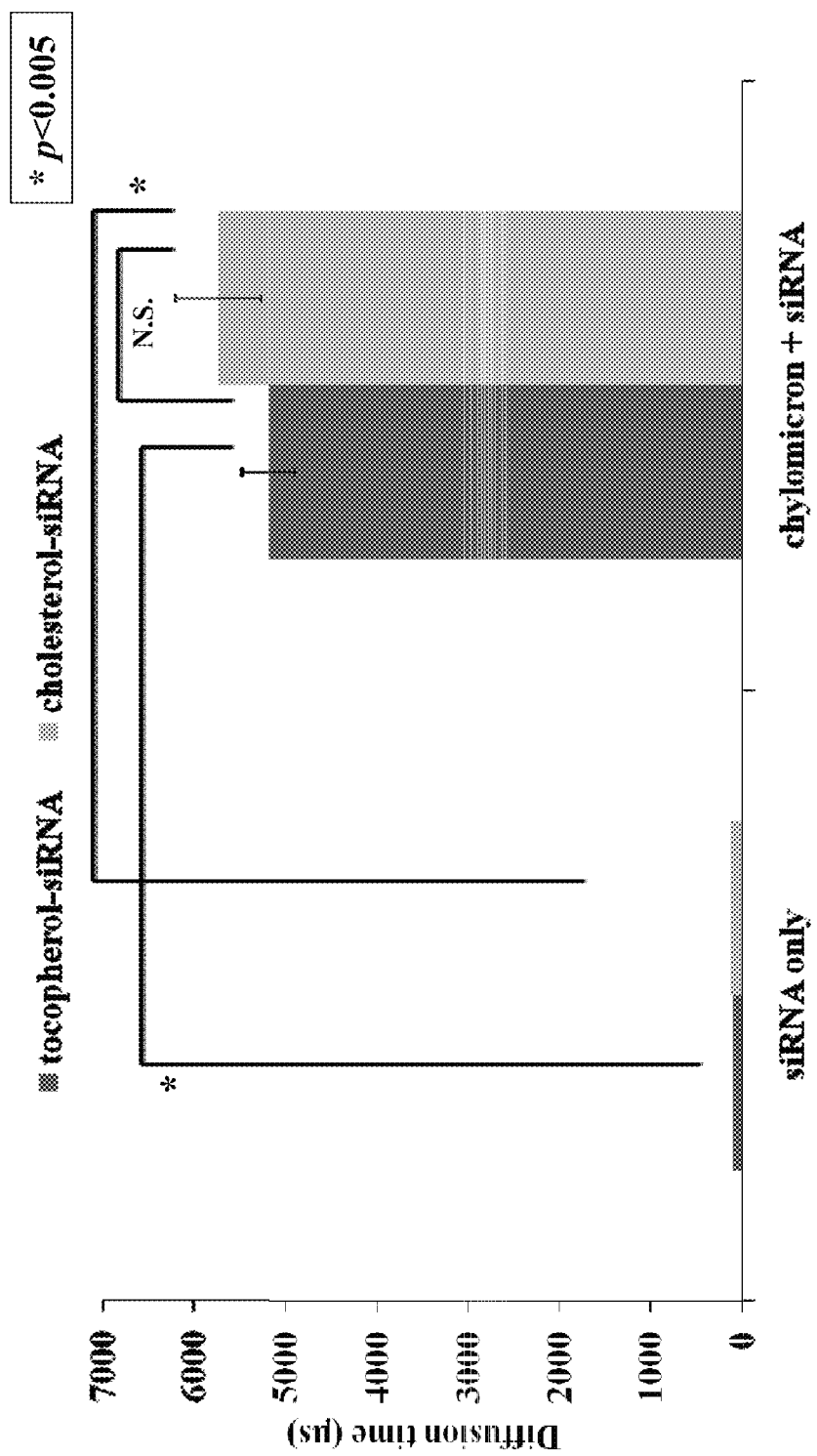

FIG. 7 This figure shows the interaction of a Toc-siRNA or Cho-siRNA and a lipoprotein (the results of a fluorescence correlation spectroscopy).

Figure 8:
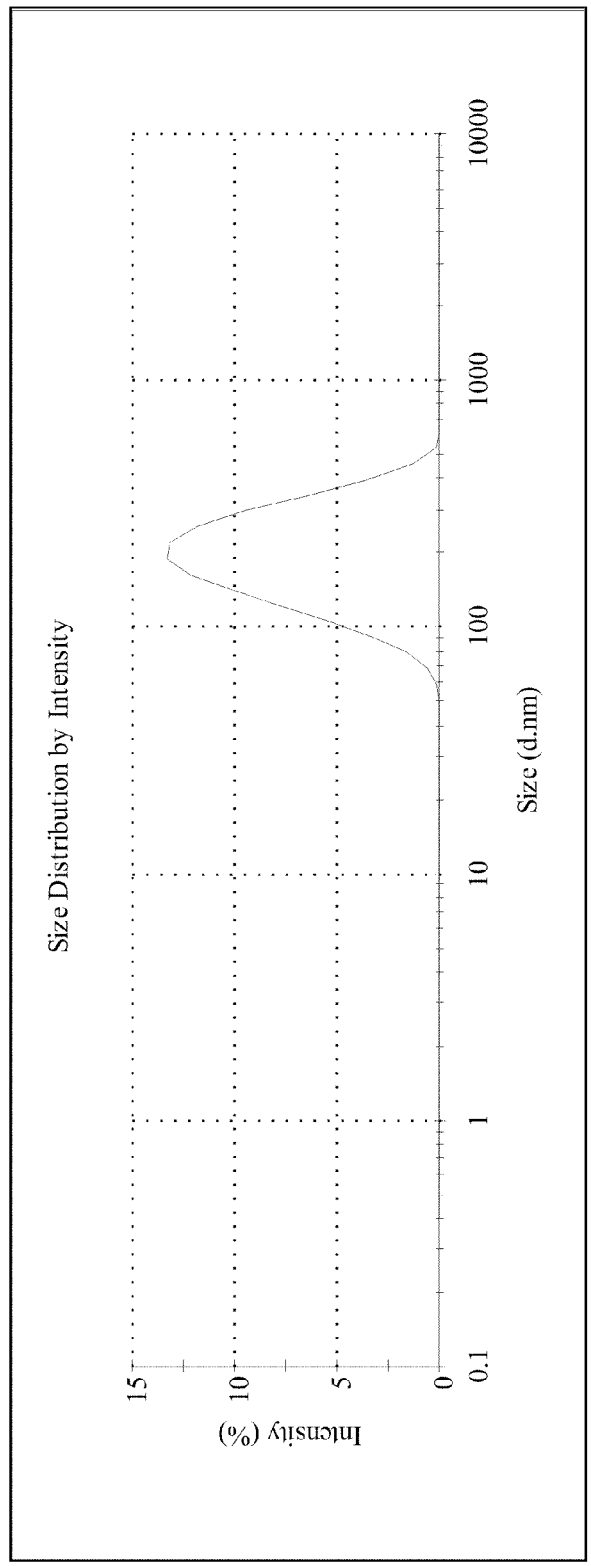

FIG. 8 This figure shows the results of measurement of the diameter of chylomicron by dynamic light scattering (DLS).

Figure 9:
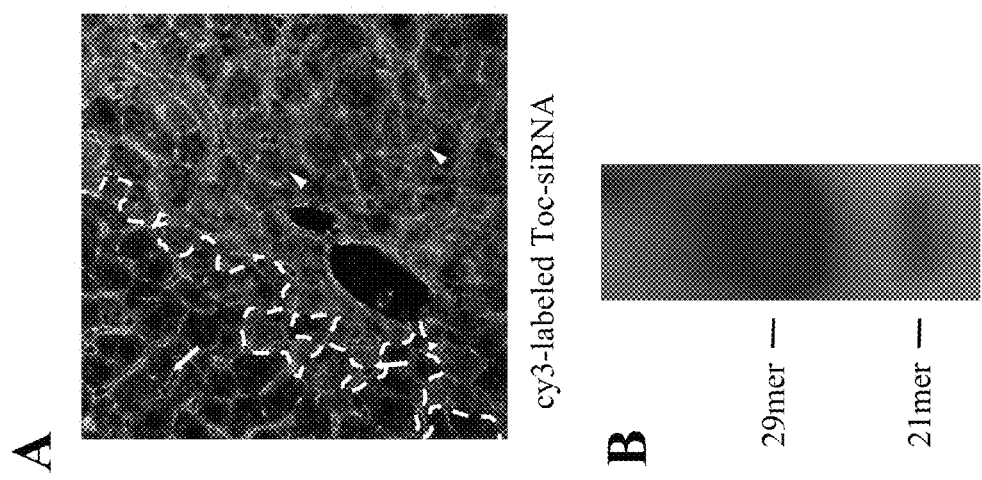

FIG. 9 This figure shows that the Toc-siRNA intravenously injected to the mouse has been taken into the liver.

A: This figure shows the result of a fluorescence microscopic observation of a liver-tissue segment after a Cy3-labeled Toc-siRNA administration.
B: This figure shows that a 27/29-mer Toc-siRNA taken into the liver was cleaved by a dicer to produce a 21-mer siRNA.

Figure 10:
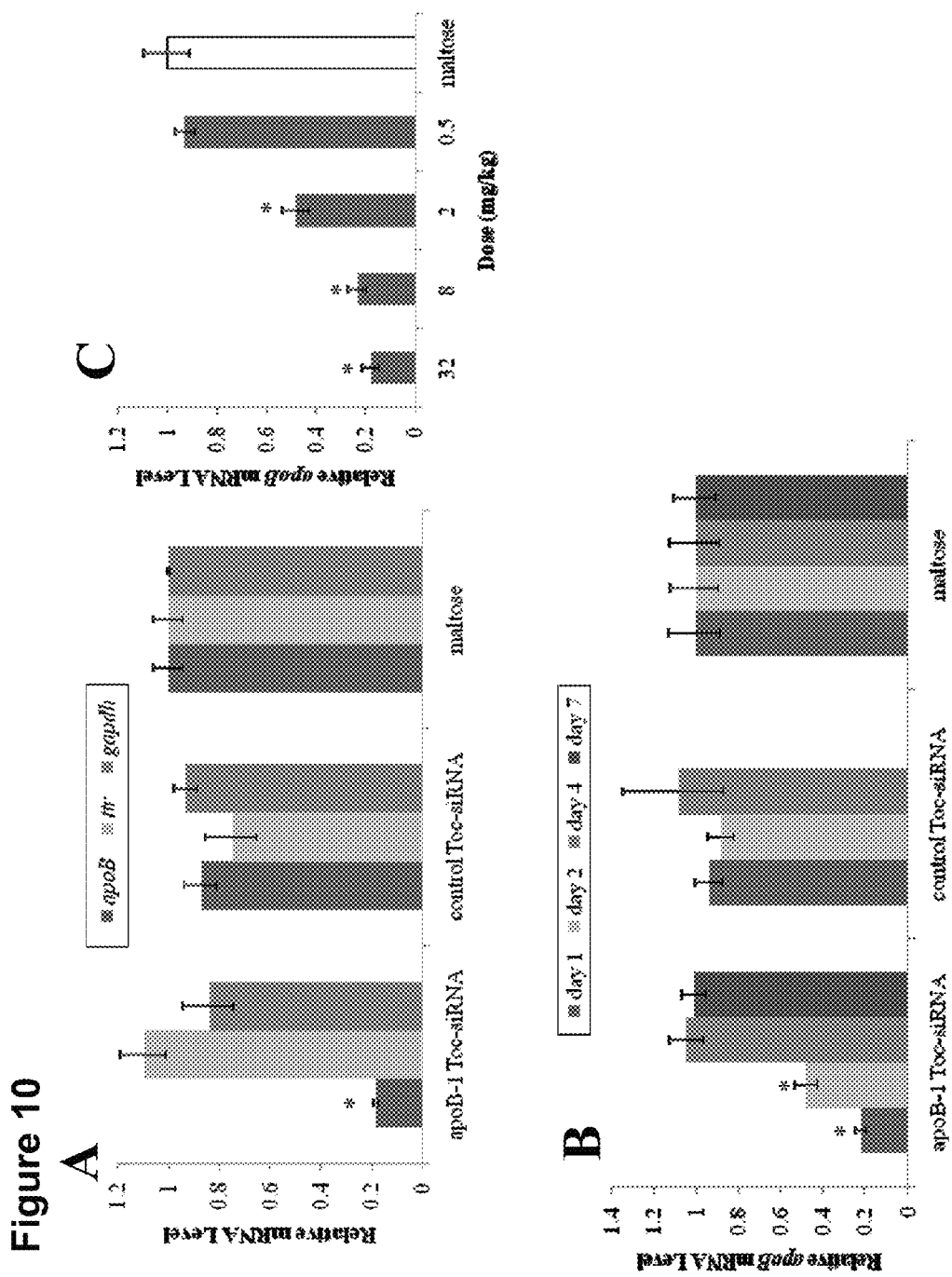

FIG. 10 This figure shows that an efficiency of the apoB mRNA-expression suppression via a Toc-siRNA in a mouse liver is gene specific as well as dose dependent. Meanwhile, the data in FIG. 10 are all shown based on n=3, means plus/minus standard deviation (SE).

A: This figure shows that a Toc-siRNA targeted to the apoB gene reduces the mRNA expression in the apoB gene-specific manner.
B: This figure shows the temporal change of the apoB-gene expression by a Toc-siRNA administration.
C: This figure shows that a Toc-siRNA has a dose-dependent expression-suppressing activity.

Figure 11:
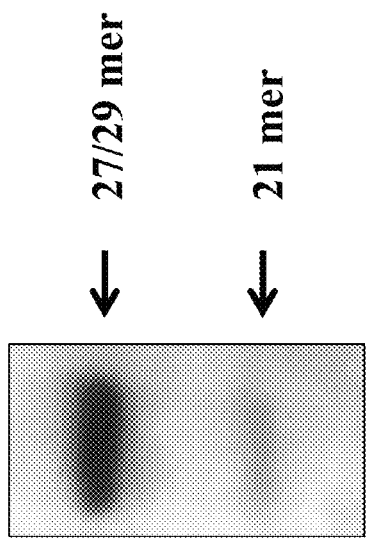

FIG. 11 This figure shows that a 27/29-mer Toc-siRNA/LP taken into a Hepa 1-6 cell line was cleaved by a dicer to produce a 21-mer siRNA.

Figures 1, 12:
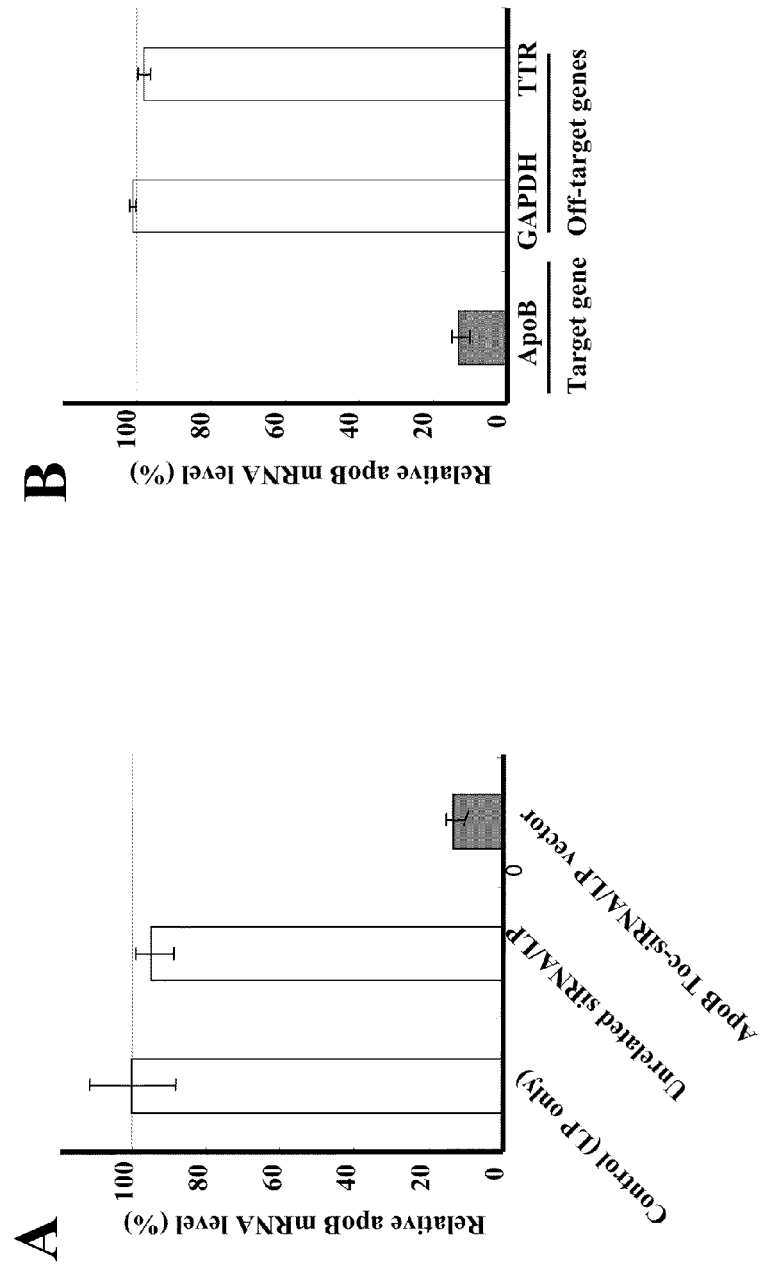
Figures 2, 12:
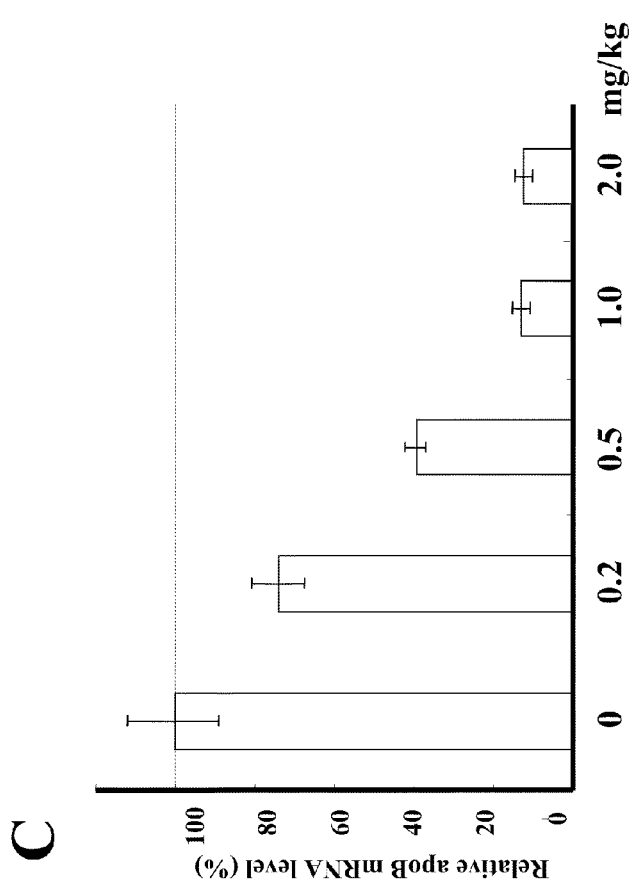

FIG. 12 This figure shows that the apoB mRNA-expression-suppression effect via Toc-siRNA/LP in a mouse liver is gene specific as well as dose dependent. Meanwhile, the data in FIG. 12 are all shown based on n=3, means plus/minus standard deviation (SE).

A: This figure shows the reduction in the apoB mRNA expression in the liver due to a Toc-siRNA/LP administration.
B: This figure shows that a Toc-siRNA/LP targeted to the apoB gene reduces the mRNA expression in the apoB-gene specific manner.
C: This figure shows that an apoB-siRNA/LP has a dose-dependent expression-suppressing activity.

Figure 13:
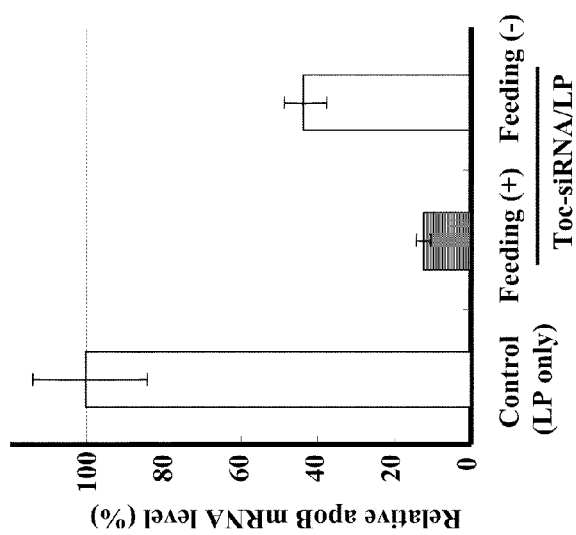

FIG. 13 This figure shows the effect of feeding prior to a Toc-siRNA/LP administration. Meanwhile, the data in FIG. 13 are all shown based on n=3, means plus/minus standard deviation (SE).

Figure 14:
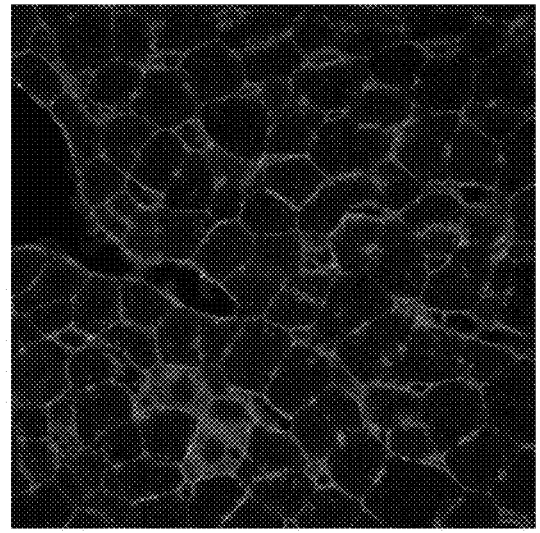
Figure 14:
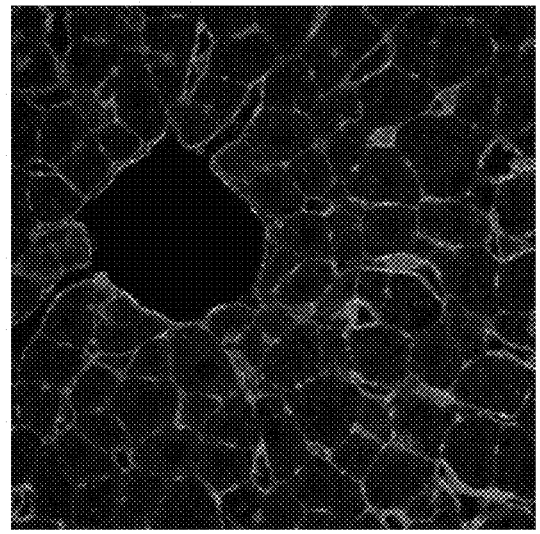

FIG. 14 This figure shows the results of confocal microscopic observations of liver segments after the rats were administered with fluorescently labeled Toc-siRNA/LP or Cho-siRNA/LP.

Left panel: This panel shows the result of using fluorescently labeled Toc-siRNA.

Right panel: This panel shows the result of using fluorescently labeled Cho-siRNA.

Figure 15:
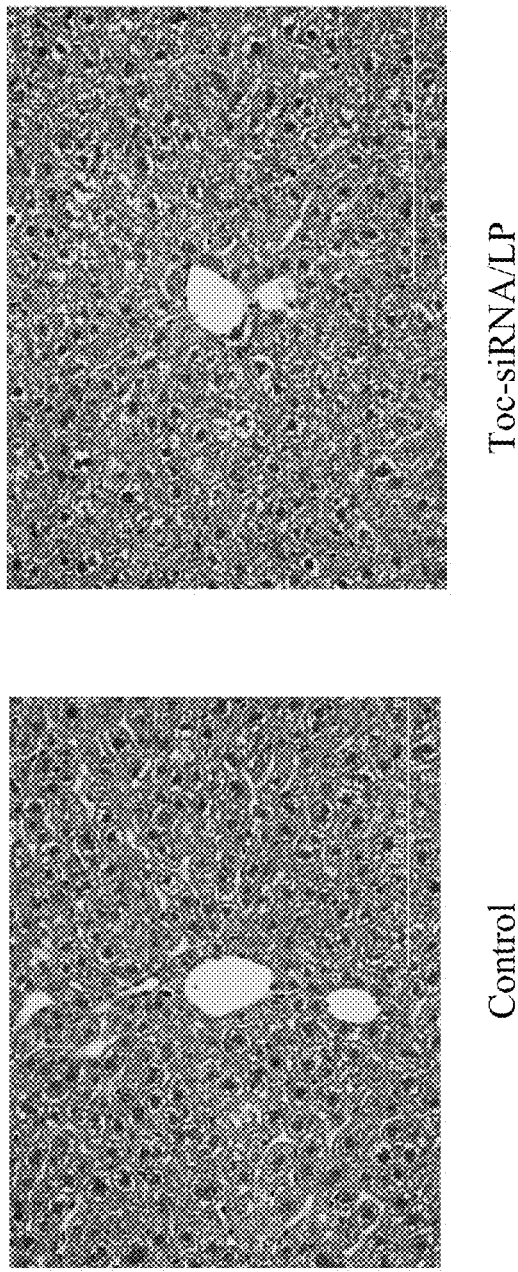

FIG. 15 This figure shows the results of a pathological analysis of the liver after a Toc-siRNA/LP administration.

Figure 16:
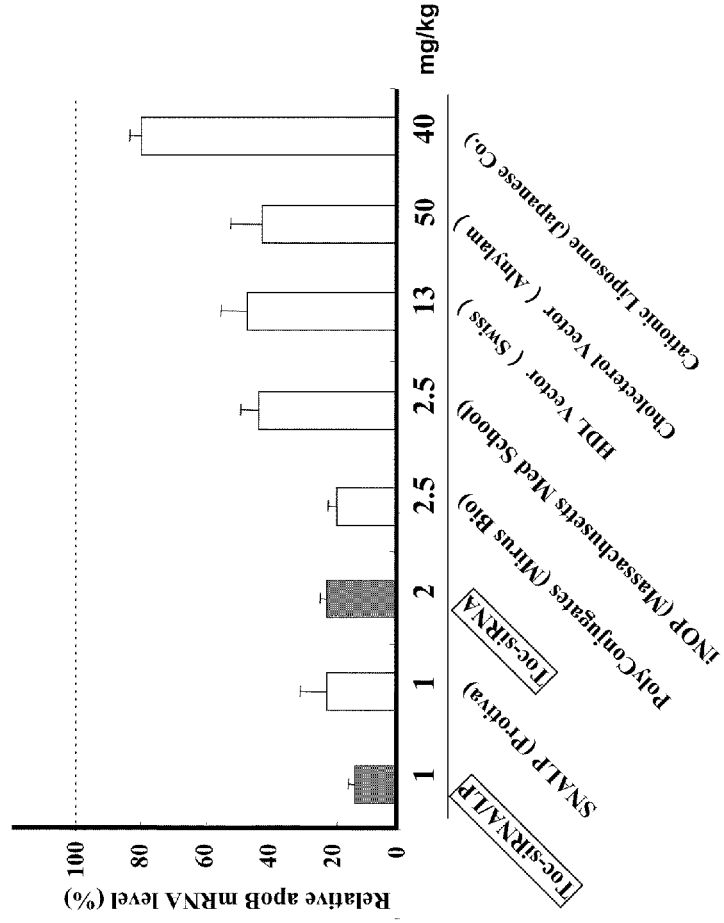

FIG. 16 This figure shows the Toc-siRNA's expression-suppressing activity for the liver apoB mRNA and the comparisons with other known non-viral vectors (however, the value for the HDL vector (Swiss) is taken from the data of the amount of the liver-apoB protein).

BEST MODE FOR CARRYING OUT THE INVENTION

The agent for suppressing a target gene expression of the present invention is characterized in that the agent contains nucleic acids for suppressing a target gene expression, to which nucleic acids an introduction substance into chylomicron is bound (hereinafter also referred to as nucleic acids to which an introduction substance into chylomicron is bound), and that the agent is administered to a vertebrate under a condition where the production of endogenous chylomicron is induced in the vertebrate.

Lipoproteins are categorized into chylomicron, VLDL, LDL, and HDL according to their specific gravities. Hepatic cells have receptors for the above lipoproteins. These receptors are: an LRP-1 receptor that binds a chylomicron remnant which is a chylomicron metabolite; an LDL receptor that binds LDL; and an SR-B1 receptor that binds HDL. Each lipoprotein is taken into cells by receptor-mediated endocytosis.

Endogenous lipids are constantly taken in by LDL-LDL receptors and HDL-SR-B1 receptors, whereas exogenous lipids including vitamin E absorbed in large amounts in a short time postprandially are taken in mainly by chylomicrons, metabolized by LPLs (lipoprotein lipase) into chylomicron remnants, and subsequently taken in by hepatic cells via chylomicron-remnant receptors (LDL receptor-related protein 1; LRP-1 receptor). An LRP-1 receptor on a hepatic cell moves to the cell surface postprandially to become activated.

This intake system into a hepatic cell that is mediated by a chylomicron remnant-LRP-1 receptor which is activated postprandially when absorbing an endogenous lipid, was used for the introduction of an siRNA.

Figure 1:
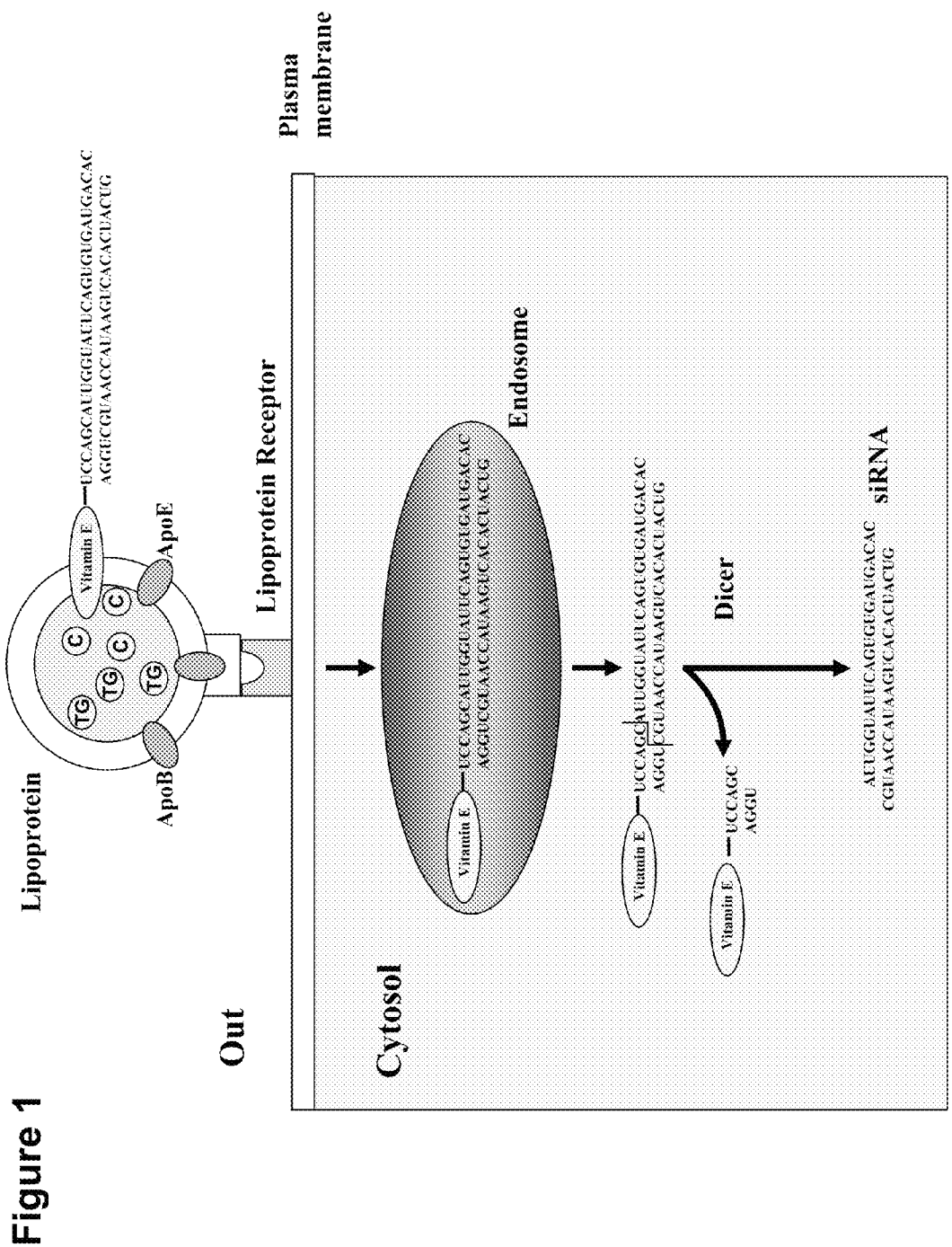
FIG. 1 This figure shows a general outline of the in vivo delivery of an alpha-tocopherol (vitamin E)-bound siRNA (Toc-siRNA).

When nucleic acids to which an introduction substance into chylomicron is bound is administered under a condition where the production of endogenous chylomicron is induced after a lipid ingestion, the introduction substance into chylomicron of the nucleic acids to which an introduction substance into chylomicron is bound, interacts with a chylomicron or the like, to form a complex of the nucleic acids to which the introduction substance into chylomicron is bound and the chylomicron. This complex of nucleic acids to which an introduction substance into chylomicron is bound and the chylomicron is taken into a cell via an LRP-1 receptor, thereby the nucleic acids for suppressing a target gene expression are taken into a cell in vivo, particularly into a hepatic cell very sufficiently. Further, since a physiological system is used, a significantly safer expression-suppressing agent can be obtained as compared to conventional suppressing agents. Meanwhile, FIG. 1 shows the outline of the delivery of the present invention in the case where vitamin E is used as an introduction substance into chylomicron and an siRNA for suppressing the expression of the mouse apoB gene as nucleic acids for suppressing a target gene expression.

The above nucleic acids for suppressing a target gene expression can be any of natural nucleotides, modified natural nucleotides, or synthetic nucleotides as long as the nucleic acids have an activity of suppressing a target gene expression (hereinafter also referred to as "an expression-suppressing activity"). The nucleic acids can be a DNA, RNA, or their chimeric forms, while by way of specific exemplifications, the nucleic acids are an siRNA, shRNA (short hairpin RNA), antisense, oligonucleotide, antagomir, nucleic acid aptamer, ribozyme, or decoy (a decoy molecule), among which an siRNA can be preferably exemplified. By way of a specific exemplification, an siRNA that is targeted to the mouse apoB gene is the siRNA consisting of the sense strand consisting of SEQ ID NO: 1 (GUCAUCACACUGAAUAC-CAAUGCUGGA) (27 mer) and the antisense strand consisting of SEQ ID NO: 2 (UCCAGCAUUGGUAUUCAGU-GUGAUGACAC) (29 mer).

Further, it is preferable that the above nucleic acids are modified so that they are not easily degraded in vivo. In particular, when the nucleic acids are an RNA, it is preferable that the nucleic acids have been subjected to an anti-RNase treatment such as a methylation treatment or thiophosphorylation treatment so that the nucleic acids are not easily degraded by RNases in a cell. More preferably, a nucleic-acid ribose is methylated at its 2' position or the skeletal binding of a nucleic acid is thiophosphorylated. The number and the position of nucleotide subjected to a methylation or thiophosphorylation may slightly affect the expression-suppressing activity of the nucleic acids and therefore, there is a preferred mode as to the number, position and the like of nucleotide that is subjected to a methylation or thiophosphorylation. This preferred mode may vary depending on the nucleic-acid sequence that is to be modified and thus can not be stated categorically, while such preferred mode can be found out easily by confirming the expression-suppressing activity of the modified nucleic acids. For example, by way of exemplification, a preferred mode of an anti-RNase treatment of the siRNA consisting of the above-mentioned SEQ ID NO: 1 and 2 comprises: the methylations of the nucleotides of nucleotide numbers 2, 5, 11, 15, 21, 24 and 25 of the sense strand (SEQ ID NO: 1) and the nucleotides of nucleotide numbers 1, 2, 5, 12, 14, 21, 24, 25, and 26 of the antisense strand (SEQ ID NO: 2) at their 2' position of the ribose; the thiophosphorylation of the skeletal binding of the nucleotide of nucleotide number 26 of the sense strand (SEQ ID NO: 1); and further methylations of the nucleotides of nucleotide numbers 3, 4, 6, 27, and 28 of the antisense strand (SEQ ID NO: 2) at their 2' position of the ribose as well as the thiophosphorylation of their skeletal bindings.

The above phrase "an activity of suppressing a target gene expression" of nucleic acids means the activity that reduces the intracellular expression of the target gene when the nucleic acids were introduced into the cell as compared to the case without such an introduction. The reduced intracellular expression of the target gene can be examined by quantifying the target gene mRNA or the protein encoded by the target gene. By way of exemplification of the suppression level of the target gene expression by the nucleic acids used in the present invention, when the nucleic acids are introduced into a given cell at 2 mg/kg, the intracellular expression of the target gene is 80% or less, more preferably 60% or less, even more preferably 40% or less, and still more preferably 20% or less at the mRNA level or at the protein level, as compared to the case without such an introduction.

When the above nucleic acids are an siRNA, the number of nucleotides of the sense strand and/or the antisense strand may be 21, while it is preferable that the number is more than 21, since an intracellular dicer cleaves between the above introduction substance into chylomicron with apart of the siRNA and the siRNA (of 21 nucleotides), thereby the siRNA of 21 nucleotides can efficiently exercise its expression-suppressing effect.

The above nucleic acids for suppressing a target gene expression can be designed by a known method based on the information on the target gene sequence, or the part of the target gene sequence to which a transcription factor can bind. For example, nucleic acids for suppressing a target gene expression can be designed using the method described in Japanese Laid-Open Patent Application No. 2005-168485 when the nucleic acids are an siRNA, the method described in Nature, 1990, 346(6287):818-22 when the nucleic acids are a nucleic-acid aptamer, and the methods described in FEBS Lett, 1988, 239, 285; Tanpakushitsu-kakusan-kouso (protein-nucleic acid enzyme), 1990, 35, 2191; and Nucl Acids Res, 1989, 17, 7059 when the nucleic acids are a ribozyme. Further, an antisense oligonucleotide, antagomir, or a decoy can be designed easily respectively based on the information on the target gene sequence, and the part of the target gene sequence to which a transcription factor can bind.

The above nucleic acids can be prepared using a known method or the like. For example, antisense oligonucleotide or a ribozyme can be prepared by determining the target sequence of an mRNA or early transcription product based on the cDNA sequence or genomic DNA sequence of the target gene and synthesizing the sequence complementary to the target sequence using a commercially available DNA/RNA automatic synthesizer (Applied Biosystems, Beckman and the like). Further, a decoy or siRNA can be prepared by synthesizing a sense strand and an antisense strand respectively with a DNA/RNA automatic synthesizer, denaturing the strands in an appropriate annealing buffer solution at about 90° C. to about 95° C. for about 1 minute, and annealing at about 30° C. to about 70° C. for about 1 to about 8 hours and the like. Further, a nucleic-acid aptamer can be prepared by the method described in Japanese Laid-Open Patent Application No. 2007-014292.

The above introduction substance into chylomicron is not particularly limited as long as the substance can be taken into lipoproteins such as a chylomicron, and the preferred introduction substances are: fat-soluble substances such as carbon hydrides, higher alcohols, higher alcohol esters, higher fatty acids, higher fatty acid esters, sterols (in particular, cholesterols) and sterol esters; peptides such as cell permeable peptides apolipoproteinsconjugate; and lipid-like molecules such as addition of alkylacrylatesor alkyl-acrylamides to primary or secondary amines. Among these, a fat-soluble vitamin, which is an exogenous lipid that cannot be synthesized in vivo is more preferred, and vitamin E is particularly preferred because it is safer.

As the above vitamin E, tocopherols represented by the following general formula (1) or tocotrienols represented by the following general formula (2), or mixtures containing two or more kinds of these compounds can be preferably exemplified:

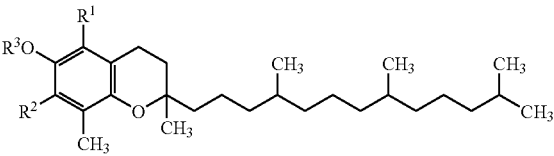

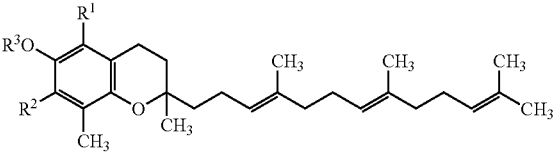

(wherein $R^1$ and $R^2$ represent a hydrogen atom or a methyl group, and $R^3$ represents a hydrogen atom or a carboxylic acid residue). Among these, particularly preferred are: an alpha-tocopherol (in general formula (1), $R^1$=methyl group, $R^2$=methyl group, and $R^3$=hydrogen atom); beta-tocopherol (in general formula (1), $R^1$=methyl group, $R^2$=hydrogen atom, and $R^3$=hydrogen atom); gamma-tocopherol (in general formula (1), $R^1$=hydrogen atom, $R^2$=methyl group, and $R^3$=hydrogen atom); sigma-tocopherol (in general formula (1), $R^1$=hydrogen atom, $R^2$=hydrogen atom, and $R^3$=hydrogen atom); alpha-tocotrienol (in general formula (2), $R^1$=methyl group, $R^2$=methyl group, and $R^3$=hydrogen atom); beta-tocotrienol (in general formula (2), $R^1$=methyl group, $R^2$=hydrogen atom, and $R^3$=hydrogen atom); gamma-tocotrienol (in general formula (2), $R^1$=hydrogen atom, $R^2$=methyl group, and $R^3$=hydrogen atom); sigma-tocotrienol (in general formula (2), $R^1$=hydrogen atom, $R^2$=hydrogen atom, and $R^3$=hydrogen atom); and acetate esters and succinates of the above compounds. Among the above, an alpha-tocopherol and gamma-tocopherol are particularly preferred. Further, anyone of d-, l-, and dl-form of vitamin Es may be used likewise.

Meanwhile, a combination of two or more kinds of the above introduction substances into chylomicron may be used. In addition, the introduction substance into chylomicron may be either a natural substance or a synthetic substance.

The bond between the above introduction substance into chylomicron and the nucleic acids may be a direct bond or an indirect bond by another substance mediating between them. Preferably, the bond is directly formed by a chemical bond such as a covalent bond, ionic bond, or hydrogen bond, among which a covalent bond provides a more stable bond and therefore can be exemplified particularly preferably.

The method of binding the introduction substance into chylomicron and the nucleic acids is not particularly limited. For example, when an introduction substance into chylomicron and nucleic acids are covalently bound, it is preferable that the covalent bond is formed according to the method described in Tetrahedron Letters 33; 2729-2732, 1992, and when an ionic bond or a hydrogen bond is utilized, it is preferable to allow an arginine residue having a positive charge to bind to an introduction substance into chylomicron and to utilize an ionic bond or hydrogen bond between this positive charge of the arginine residue and a negative charge of the nucleic acids such as an siRNA to form the bond. Meanwhile, from the viewpoint of obtaining a more stable binding to the nucleic acids, the number of arginine residues bound to an introduction substance into chylomicron is preferably at least two, more preferably at least three, and even more preferably at least four.

In addition to the above essential components, the expression-suppressing agent of the present invention can be formulated with components used in medicinal products as needed, such as lipoprotein, water, oil solution, wax, silicone, surfactant, alcohol, polyhydric alcohol, water-soluble high-molecular thickener, pH adjuster, flavor, antioxidant, chelating agent, pigment, antiseptic agent, and other medicinal components as well as inorganic or organic components, within the qualitative and quantitative range that does not affect the effect of the present invention.

The expression-suppressing agent of the present invention can be formulated using the above essential components and optional components as needed according to a common method, into various dosage forms including solid formulations such as powder, granules, tablets, and capsules; liquid formulations such as syrup, emulsion, and injections (including a subcutaneous injection, intravenous injection, intramuscular injection, and infusion); sustained-release formulations such as sublingual tablets, buccals, troches, and microcapsules; intraoral rapid-disintegrant; and suppository, among which injections can be preferably exemplified.

The expression-suppressing agent of the present invention is administered to a vertebrate under a condition where the production of endogenous chylomicron is induced in the vertebrate with a view to improving the intake efficiency into a cell, of nucleic acids to which an introduction substance into chylomicron is bound and thus increasing the suppression efficiency of a target gene expression. The condition where the production of endogenous chylomicron is induced in the vertebrate is not limited as long as the above object can be achieved, while a preferred condition is within 12 hours (for example, within 10 hours, within 8 hours, within 6 hours, within 4 hours, within 2 hours, and within 1 hour) after an oral lipid administration to a vertebrate. The lipid can be orally administered either as a lipid itself or in the form of a lipid-containing meal. It is preferable that the subject of administration is allowed to be in a state of starvation prior to an induction of endogenous chylomicron. The detailed action mechanism has not been revealed how a lipid administration, and what is more, allowing the subject of administration to be in a state of starvation, improve the intake efficiency into a cell, of nucleic acids to which an introduction substance into chylomicron is bound. However, considering the fact that an LRP-1 receptor on a hepatic cell, which is involved in lipoprotein intake, is known to be expressed at a higher level on cell membranes and to be activated due to an oral lipid ingestion or by insulin (Mol. Pharmacol. 2007 Jul. 3; 17609417), it is believed that a lipid ingestion or the like causes the receptor involved in lipoprotein intake to be expressed at a higher level as well as activated, resulting in the increased chylomicron introduction into a hepatic cell and thereby improves the intake efficiency into a hepatic cell, of nucleic acids to which an introduction substance into chylomicron is bound.

Meanwhile, the above phrase "a state of starvation" refers to a state in which no food or drink (except a calorie-free drink or food such as water) has been ingested for a certain period of time including, for example, a state in which the subject of administration has not been given any food at least for 6 hours, preferably for at least 8 hours, more preferably at least for 12 hours, and even more preferably at least for 24 hours.

Sufficient LPLs are required in order for the administered chylomicrons to be metabolized into chylomicron remnants that will be rapidly taken into hepatic cells. Therefore, it is preferable to administer LPL inhibitor such as Triton (for example, by an intravenous injection) before administering lipid (or a lipid-containing product) to increase the concentration of chylomicrons. Further, LPLs act on hepatic cells and causes them to take in vitamin E. With an administration of heparin, LPLs bound to heparan sulfate on the endothelial cell surface can be freed into the blood. Therefore, it is preferable to administer LPL and/or heparin to a vertebrate before nucleic acids are administered.

Further, the expression-suppressing agent of the present invention can be administered by mixing ex vivo with a chylomicoron-rich lipoprotein. The lipoprotein is not particularly limited as long as the lipoprotein contains a lipid and apoprotein, and can be taken into a cell through any lipoprotein receptors. A preferred lipoprotein contains cholesterol, triglyceride, phospholipid and apoprotein. The lipoprotein may be collected from a living body, a recombinant, or chemically synthesized, while a living body-derived lipoprotein is preferred from the viewpoint of achieving a higher level of safety. Moreover, from the viewpoint of further reducing side-effects due to an immunological allergic reaction, it is more preferable that the lipoprotein is collected from an individual who is the subject of administration itself or from an individual of the same species as the subject of administration of the expression-suppressing agent.

By way of specific and preferred exemplification, the above living body-derived lipoprotein is: a chylomicron formed on the intestinal moucosa by a lipid absorbed in vivo together with an apoprotein; or a chylomicron remnant produced from the chylomicron degraded by vascular endothelial lipoprotein lipase. Among these, the chylomicron is preferably exemplified. The above apoprotein is not particularly limited and by way of preferred exemplification, the apoprotein is an apoB protein or apoE protein.

A lipoprotein containing a chylomicron used in the present invention may be collected from a living body, prepared from a synthetically-obtained substance, or a mixture thereof. As for a method of collecting a lipoprotein from a living body, the blood may be collected several hours after a lipid ingestion, while by way of preferred exemplification, 0.08 to 0.4 g/kg of Triton is injected intravenously, subsequently 5 to 25 ml/kg of high-protein/lipid solution (10 mg/ml of albumin, 40 mg/ml of triolein, and 40 mg/ml sodium taurocholate) is administered orally to a living body, and then blood is collected after 3 to 12 hours. Further, by way of preferred exemplification, the method of preparing the above chylomicron-rich lipoprotein from a living body is, for example, a method where serum collected from a living body several hours after a lipid ingestion is added with a solution (a solution containing 11.4 g of NaCl, 0.1 g of EDTA, and 1 ml of 1N NaOH per 1 liter of water; specific gravity 1.006) in the same volume as the serum, and the solution is centrifuged to provide a suspension from which the supernatant is collected.

Further, the expression-suppressing agent of the present invention can be administered orally or parenterally depending on the type of the above-mentioned formulations, while from the viewpoint of achieving the expression-suppressing effect more quickly and efficiently, the expression-suppressing agent is preferably administered parenterally, more preferably administered by an injection, and even more preferably administered by an intravenous injection.

The applied dose of the expression-suppressing agent of the present invention varies depending on age, weight, symptom of the subject of administration, the kind of disease affecting the subject of administration, and the sequence of siRNA or the like contained in the expression-suppressing agent. Generally, 0.1 to 30 mg/kg (siRNA weight basis) can be administered by dividing the amount into 1 to 3 separate doses a day.

The target disease of the expression-suppressing agent of the present invention is not particularly limited as long as the suppression of a particular gene could lead to the treatment of the disease. The above disease is caused by the expression of a particular pathologic target gene, and by way of particularly preferred exemplification, the disease is viral hepatitis caused by an elevated expression of hepatitis virus gene or the familial amyloid neuropathy caused by the expression of a transthyretin gene variant.

The subject of administration in the present invention is not particularly limited as long as the subject is an animal. By way of preferred exemplification, the subject of administration is vertebrates, while animals belonging to mammals or birds are more preferably exemplified, among which, humans, rats, mice, pigs, rabbits, dogs, cats, monkeys, horses, cows, goats, and sheep can be even more preferably exemplified and human is particularly preferably exemplified.

Further, the expression-suppressing agent of the present invention can be used as an active ingredient of the pharmaceutical composition of the present invention. The pharmaceutical composition of the present invention is characterized in that it contains the expression-suppressing agent of the present invention as an active ingredient.

In the present invention, the method for delivering nucleic acids into a cell (hereinafter also referred to as the delivery method of the present invention) is characterized in that the method comprises process (C) of administering to a vertebrate nucleic acids for suppressing a target gene expression, to which nucleic acids an introduction substance into chylomicron is bound, under a condition where the production of endogenous chylomicron is induced in the vertebrate. When nucleic acids to which an introduction substance into chylomicron are bound are administered to a vertebrate under a condition where the production of endogenous chylomicron is induced in the vertebrate, the introduction substance into chylomicron of the nucleic acids to which an introduction substance into chylomicron is bound, interacts with a lipoprotein to form a complex of the nucleic acids to which an introduction substance into chylomicron is bound and the lipoprotein. This complex of the nucleic acids to which an introduction substance into chylomicron is bound and the lipoprotein, is taken into a cell via a lipoprotein receptor, and therefore has enabled a very efficient in vivo intracellular delivery of nucleic acids for suppressing a target gene expression. The use of the delivery method of the present invention has also enabled nucleic acids to be delivered appreciably more safely as compared to conventional methods even in vivo. The terms "nucleic acids for suppressing a target gene expression, to which nucleic acids an introduction substance into chylomicron is bound" and "a lipoprotein" in the delivery method of the present invention have meanings as described above.

In the delivery method of the present invention, the method of administering to a vertebrate nucleic acids to which an introduction substance into chylomicron is bound, under a condition where the production of endogenous chylomicron is induced in the vertebrate, is not particularly limited, and the nucleic acids can be administered by the same method as the expression-suppressing agent of the present invention.

Tissues that can be delivered nucleic acids to which an introduction substance into chylomicron is bound by the delivery method of the present invention is not particularly limited, and the nucleic acids to which an introduction substance into chylomicron is bound can be delivered in vivo to any tissues such as liver, brain, peripheral nerves, lungs, intestinal tract, pancreas, kidneys, cardiac muscles, and skeletal muscles.

Figure 2:
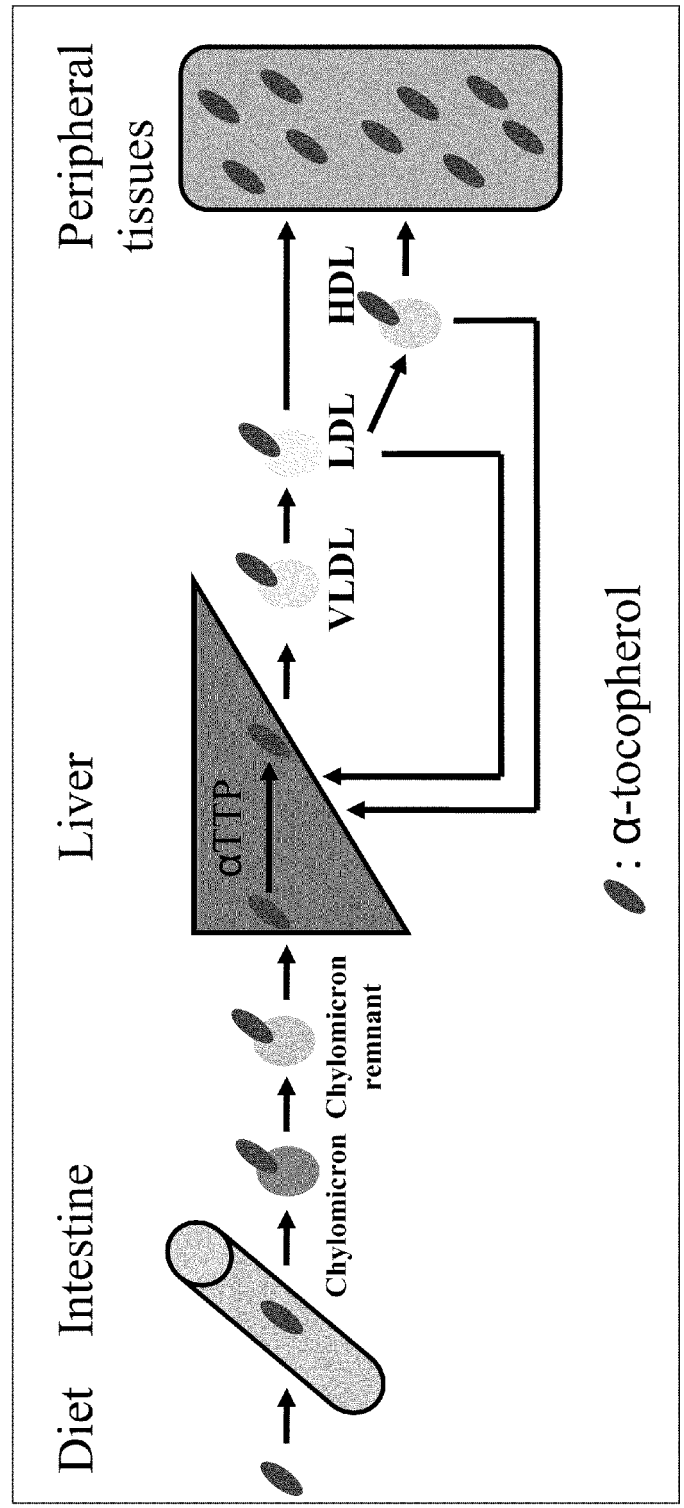
FIG. 2 This figure shows the transportation of an alpha-tocopherol between different types of tissues.

FIG. 2 shows a diagram of an alpha-tocopherol transportation in the body to show that nucleic acids to which a lipid-soluble substance is bound can be delivered in vivo to each tissue by the delivery method of the present invention.

As shown in FIG. 2, an alpha-tocopherol contained in food or drink is absorbed by small intestines and further, mainly taken into a chylomicron which is a kind of lipoprotein. This chylomicron is metabolized into a chylomicron remnant by lipoprotein lipase (LPL) and is transported to the liver by this chylomicron remnant. In the hepatic cytoplasm, an alpha-tocopherol is taken into a VLDL (very low-density lipoprotein) by an alpha-TTP (alpha-Tocopherol Transfer Protein). Subsequently, the VLDL containing an alpha-tocopherol is secreted into the blood and metabolized into an LDL (low-density lipoprotein) or HDL (high-density lipoprotein cholesterol) to form an alpha-tocopherol-containing LDL or HDL. These LDL and HDL are transported by blood to each tissue so that the alpha-tocopherol is efficiently taken into various tissues through a receptor-mediated endocytosis that is mediated by a lipoprotein receptor existing on each tissue (for example, an LRP-1 receptor, LDL receptor, HDL receptor or the like). Incidentally, even when a substance other than alpha-tocopherol is used as an introduction substance into chylomicron in the present invention, nucleic acids to which an introduction substance into chylomicron is bound of the present invention together with a lipoprotein are efficiently taken into a cell of each tissue through an endocytosis mediated by a lipoprotein receptor.

The delivery method of the present invention is not particularly limited as long as the method comprises the above process (C), while from the viewpoint of enhancing the delivery efficiency of the nucleic acids so as to achieve an increased suppression efficiency of a target-gene expression, it is preferable that, before an administration of the nucleic acids to a vertebrate under a condition where the production of endogenous chylomicron is induced, the method comprises administering heparin and/or LPL to a subject of administration (process (B)); and that, before process (C), the method further comprises allowing a vertebrate to be in a state of starvation (process (A)). The above term "a state of starvation" refers to a state where no food or drink is ingested for a certain period of time (except calorie-free food or drink such as water). The above state of starvation comprises the state where no food is given to the subject of administration, for example, at least for 6 hours, preferably at least for 8 hours, more preferably at least for 12 hours, and even more preferably at least for 24 hours.

The method for treating a disease of the present invention (hereinafter also referred to as the treatment method of the present invention) is characterized in that the method comprises process (C) of administering to a vertebrate nucleic acids for suppressing a target gene expression, to which nucleic acids an introduction substance into chylomicron in bound, under the condition where the production of the endogenous chylomicron is induced in the vertebrate. When nucleic acids to which an introduction substance into chylomicron is bound are administered to a vertebrate under a condition where the production of endogenous chylomicron is induced in the vertebrate, as mentioned above, the nucleic acids to which a lipid-soluble substance is bound are taken into a cell in vivo very efficiently, thereby an effect of suppressing the target gene expression is sufficiently exhibited in an appreciably safer manner as compared to conventional methods. Consequently, a superior therapeutic effect is obtained against the disease. In the treatment method of the present invention, the phrases "nucleic acids for suppressing a target gene expression, to which nucleic acids an introduction substance into chylomicron is bound" and "a chylomicron-rich lipoprotein" have meanings as described above.

In the treatment method of the present invention, the method of administering to a vertebrate nucleic acids to which an introduction substance into chylomicron is bound, under a condition where the production of endogenous chylomicron is induced in the vertebrate is not particularly limited, and the nucleic acids can be administered by the same method as the expression-suppressing agent of the present invention. Further, the target disease of the treatment method of the present invention is not particularly limited as long as the disease is caused by an elevated expression of a given gene. By way of specific exemplification, the disease is same as the above target diseases of the expression suppressing agent of the present invention.

The present invention will be described in detail with reference to the following examples, while the scope of the present invention will not be limited to these exemplifications.

EXAMPLE

Example 1

Cell Culture

A mouse hepatic-cancer cell line (Hepa 1-6 cell line) used in the experiment described hereinbelow was maintained in the following manner.

A mouse hepatic-cancer cell line (Hepa 1-6 cell line) was maintained under the condition of 37° C. and 5%-by-mass of $CO_2$, using a growth medium (DMEM: Sigma) added with 10%-by-mass of bovine fetal serum, 100 units/ml of penicillin and 100 micro-g of streptomycin.

Example 2

Separation of Lipoprotein-Rich Serum with High Chylomicron Content

The lipoprotein-rich serum with high chylomicron content used in the experiment described hereinbelow was separated and adjusted in the following manner.

12- to 14-week old ICR mice (Charles River Laboratories: U.S.A) were intravenously injected at the tail with 0.4 g/kg of Triton WR-1339 (Nacalai Tesque, Inc.: Kyoto, Japan). 10 minutes after the injection, the above mice were orally administered with 0.5 ml of protein-rich fluid food containing 5 mg of bovine serum albumin (Sigma), 20 mg of triolein (Wako Pure Chemical Industries, Ltd.: Tokyo, Japan), and 20 mg of sodium taurocholate (Wako Pure Chemical Industries, Ltd.: Tokyo, Japan). To the serum collected from the mice 3-12 hours after the oral administration of the protein-rich fluid food, a solution (a solution containing 11.4 g of NaCl, 0.1 g of EDTA, 1 ml of 1N NaOH per 1 liter of water; specific gravity 1.006) was added in the same volume as the serum, which was then centrifuged at 26,000 g for 30 minutes under the condition of 16° C. The upper one-sixth of the resultant suspension was collected as a lipoprotein-rich serum. Triglyceride in this lipoprotein-rich serum was measured using Triglyceride E-TST kit (Wako Pure Chemical Industries, Ltd.: Tokyo, Japan), and the amount used was adjusted as desired.

Example 3

Isolation of the Liver of the Mice Administered with Toc-siRNA and the Like The liver of the mice administered with Toc-siRNA and the like used in the experiment described hereinbelow was prepared in the following manner.

First, 4-week old ICR mice (Charles River Laboratories: U.S.A) were provided. The above mice were fasted for 24 hours prior to the administration of Toc-siRNA and the like. Then, the mice were intravenously injected at the tail with 0.08 to 0.2 g/kg of Triton. Subsequently, the above mice were orally administered with 0.5 ml of protein-rich fluid food containing 250 micro-g of bovine serum albumin (Sigma) and 1 mg of triolein (Wako Pure Chemical Industries, Ltd.: Tokyo, Japan). Ten minutes to 10 hours from the administration of the protein-rich fluid food, the mice were given at the tail a single intravenous administration of 0.25 ml of a 10%-by-mass maltose solution containing Toc-siRNA or the like. Ten minutes before administration of Toc-siRNA, the mice were intravenously injected at the tail with 8 to 10 units of heparin. Then, the mice were anesthetized as desired by an intraperitoneal administration of 60 mg/kg of pentobarbital, killed by perfusing a PBS solution transcardially, and the liver was taken out.

Example 4

Quantitative RT-PCR

Unless otherwise described, the quantitative RT-PCR performed in the experiment described hereinbelow was performed in the following manner.

The total RNA was extracted from the cultured cells or tissues of the mice using Isogen (Nippon Gene Co., Ltd.: Tokyo). By using Superscript III and Random hexamers (Invitrogen) as directed by the accompanying protocol, the above RNA was reversely transcribed to obtain the DNA which is complementary to the RNA. A quantitative RT-PCR was performed using 0.5-micro-1 of the above-mentioned complementary DNA, a predetermined primer and TaqMan Universal PCR Master Mix (Applied Biosystems) as directed by the accompanying protocol. In the above quantitative RT-PCR, the amplification was performed using ABI PRISM 7700 Sequence Detector (Applied Biosystems) by repeating 40 cycles each consisting of a denaturalization at 95° C. for 15 seconds and an annealing at 60° C. for 60 seconds. Meanwhile, the primer for the mouse apoB gene, the primer for the GAPDH gene, and the primer for the TTR (Transthyretin) gene used as the above-mentioned predetermined primers were designed by Applied Biosystems.

Example 5

Northern Blot Analysis

Unless otherwise described, the northern blot analysis performed in the experiment described hereinbelow was performed in the following manner.

Using MirVana (Ambion, Inc.: Austin, Tex., U.S.A), the total RNA was extracted from the Hepa 1-6 cell line or the mouse liver. The extracted RNA was concentrated using Ethachinmete (Nippon Gene Co., Ltd.: Tokyo, Japan). From the obtained RNA, 2 micro-g was electrophoretically separated with 14%-by-mass polyacrylamide gel (containing urea) and then transferred onto a Hybond-N+ membrane (Amersham Biosciences, Inc.: Piscataway, N.J., U.S.A).

Meanwhile, as a probe for the northern blotting, an siRNA antisense strand, fluorescently labeled with Gene Images 3'-oligo labeling kit (Amersham Biosciences, Inc.), was provided.

Using the above-mentioned transfer membrane and the probe and the like, a northern blot analysis was performed in accordance with a common method. The signals from the above fluorescent labels were visualized using Gene Images CDP-star detection Kit (Amersham Biosciences, Inc.)

Example 6 siRNA Synthesis

Based on the mouse apoB gene sequence, an siRNA targeted to the mouse apoB gene was designed. The nucleotide sequence of the sense strand (27 mer) of this siRNA is shown in SEQ ID NO: 1 (GUCAUCACACUGAAUAC-CAAUGCUGGA) and the nucleotide sequence of the antisense strand (29 mer) in SEQ ID NO:2 (UCCAGCAUUG-GUAUUCAGUGUGAUGACAC). These nucleotide sequences of the sense strand and the antisense strand were synthesized in accordance with a common method.

Subsequently, these nucleotide sequences were modified for an improved stability to in vivo RNases. More specifically, the nucleotides of nucleotide numbers 2, 5, 11, 15, 21, 24, and 25 of the siRNA sense strand (SEQ ID NO: 1) and the nucleotides of nucleotide numbers of 1, 2, 5, 12, 14, 21, 24, 25, and 26 of the antisense strand (SEQ ID NO: 2) were subjected to 2'-O-ribose methylation; the skeletal bond of the nucleotide of nucleotide number 26 of the sense strand (SEQ ID NO: 1) was subjected to thiophosphorylation; and further, the nucleotides of nucleotide numbers 3, 4, 6, 27, and 28 of the antisense strand (SEQ ID NO: 2) were subjected to 2'-ribose methylation as well as thiophosphorylation of their skeletal bond.

Subsequently, in accordance with the method described in a literature (Tetrahedron Letters 33; 2729-2732. 1992), an alpha-tocopherol (Tokyo Chemical Industry Co., Ltd.: Tokyo, Japan) was bound to the 5' terminal of the siRNA antisense strand (FIG. 4).

Figure 3:
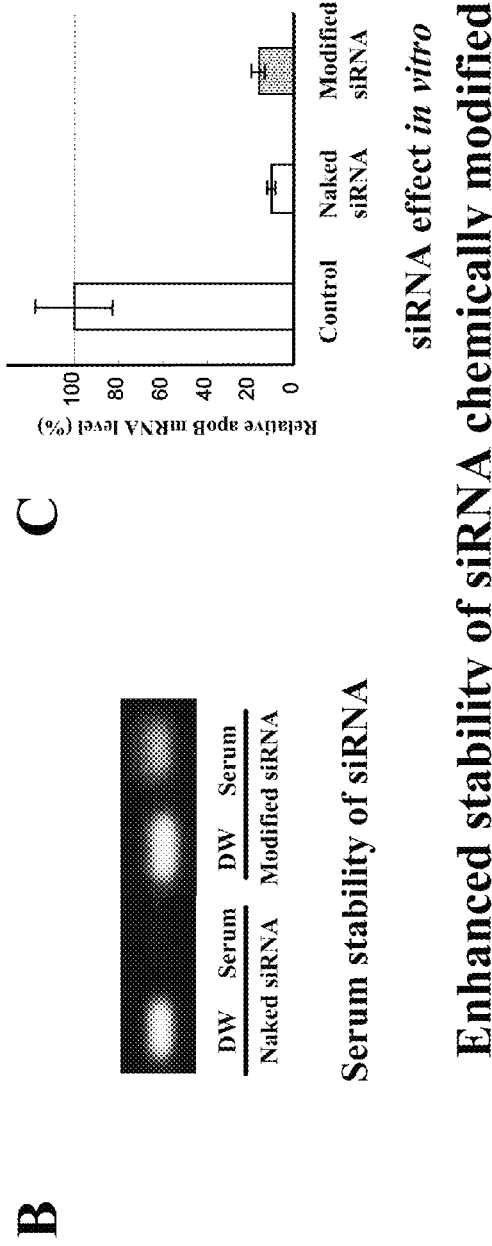
FIG. 3 This figure shows the stability and the expression-suppressing activity of an siRNA chemically modified by a thiophosphorylation of the skeletal bond and 2'-O-methylation of the ribose of the nucleotides.

The above antisense-strand nucleotide sequence to which an alpha-tocopherol is bound and the sense-strand nucleotide sequence were annealed in an RNase-free distilled water (DW) at 95° C. for 1 minute and then incubated at 37° C. for 1 hour, thereby the alpha-tocopherol-bound siRNA (hereinafter also referred to as "Toc-siRNA") used in the present study was obtained. Meanwhile, this siRNA has the sense-strand nucleotide sequence and the antisense-strand nucleotide sequence that are different in length as described above, and this has created a 2-mer-nucleotide overhung at the 3' terminal of the antisense strand (FIG. 3A).

Further, according to a common method, cholesterol-bound siRNA (hereinafter, also referred to as "Cho-siRNA") wherein cholesterol is bound to 5' terminal of the antisense strand of the above siRNA was prepared using 3'-cholesteryl-TEG-CPG (GlenResearch), which is a cholesterol-modification reagent for RNA.

Example 7 siRNA Stability Test

To examine the effect of the above chemical modification in Example 6 on the siRNA stability, the following experiment was performed.

First, an siRNA targeted to the mouse apoB gene and chemically modified in the above Example 6 (hereinafter also referred to as "a modified siRNA") was prepared (2 micro-g). This siRNA was incubated at 37° C. for 24 hours in distilled water (DW) or in the above lipoprotein-rich serum prepared in accordance with the method described in Example 2. A given quantity was taken from each of the obtained solutions, treated with protainase K for 1 hour, and subjected to an electorophoresis with 2%-by-mass agarose gel, respectively.

Further, in place of the above modified siRNA, an siRNA same as the above siRNA except that it had not been modified (hereinafter also referred to as "an unmodified siRNA") (2 micro-g) was used to perform an electrophoresis in the same manner.

The result of the electrophoresis is shown in FIG. 3B. As can be seen from FIG. 3B, the modified siRNA shows a significantly improved stability in the serum as compared to the unmodified siRNA (Naked siRNA). This demonstrates that the modified siRNA is more stable to RNAases contained in the serum as compared to the unmodified siRNA.

Example 8

In Vitro Activity Test of siRNA

A chemical modification of an siRNA sometimes impairs the expression-suppressing activity (silencing activity) of the siRNA. To examine the in vitro expression-suppressing activity of the above modified siRNA, the following experiment was performed.

First, the above modified siRNA (2 micro-g) targeted to the mouse apoB gene was prepared. Next, a Hepa 1-6 cell line was transfected with 10 nM of the above modified siRNA using Lipofect Amine RNAiMAX (Invitrogen). The transfected cell line was cultured for 24 hours after the transfection. From the resultant cell line, the total RNA was extracted and measured for the amount of endogenous apoB mRNA by the above quantitative RT-PCR described in Example 4.

Further, by using an unmodified siRNA or an siRNA to a non-targeted gene (control siRNA) in place of the above modified siRNA, a quantitative RT-PCR was performed in the same manner.

The results are shown in FIG. 3C. As can be seen from FIG. 3C, the modified siRNA exhibited an expression-suppressing activity which is comparable to that of the unmodified siRNA (Naked siRNA).

Example 9

Interaction of Toc-siRNA and Lipoprotein

To examine whether the Toc-siRNA is taken into a lipoprotein (LP)-rich serum with high chylomicron content, the following experiment was performed.

First, 45 micro-1 of aqueous solution of 0.4 micro-g/ml Toc-siRNA was incubated for 1 hour together with 135 micro-1 of lipoprotein-rich serum containing 2.7 mg of triglyceride prepared in accordance with the above method described in Example 2 to prepare an alpha-tocopherol-bound siRNA-containing lipoprotein (Toc-siRNA/LP) solution. This Toc-siRNA/LP solution was filtered with a centrifugal filtration unit, Micron YM-100 (Millipore) that blocks a material having the molecular weight of 100,000 or above. The solution obtained by the filtration was subjected to an electrophoresis with 2%-by-mass agarose gel and the RNA was dyed with ethidium bromide.

Further, in place of the above "Toc-siRNA/LP solution", its alpha-tocopherol bond-lacking form of "siRNA/LP solution", its lipoprotein-lacking form of "Toc-siRNA solution", and its alpha-tocopherol bond-lacking and lipoprotein-lacking form of "siRNA solution" were used to go through the same operation.

Further, for each of the above cases, a solution obtained by eluting the fraction left on the filter after the filtration was used in place of the solution obtained by the filtration, to go through the same operation.

The results of these experiments are shown in FIG. 5. The upper row in FIG. 5 shows the results of an electrophoresis of a solution obtained by eluting the fraction left on the filter (in centrifugal device) and the lower row shows the results of an electrtophoresis of a solution obtained by filtration (Filtered un-conjugated siRNA). As can be seen from the results shown in FIG. 5, siRNA is trapped by the above filter only in the case where the siRNA has been bound to an alpha-tocopherol (Tocopherol-conjugation+) and incubated with a lipoprotein-rich serum (lipoproteins+). This shows that the interaction of an siRNA and a lipoprotein is created only when the siRNA has been bound to an alpha-tocopherol (Tocopherol-conjugation+) and incubated with a lipoprotein-rich serum (lipoproteins+), and thus suggests the possibility that a Toc-siRNA is taken into a chylomicron and the like in vivo and transferred to and absorbed by each tissue via receptors such as an LRP-1 receptor.

Example 10

Interaction of Toc-siRNA or Cho-siRNA and a Lipoprotein (1) Gel Electrophoresis Experiment Rat chylomicron collected from a lymph vessel of a rat administered with high-fat food was adjusted with PBS so that the triglyceride concentration becomes 40 mg/ml and then treated with 100 μg/ml lipoprotein lipase (LPL) to obtain an aqueous solution of rat chylomicron remnant (hereinafter, referred to as CR). 10 μl of the CR aqueous solution was mixed with 2 μl of a 50 μM Toc-siRNA aqueous solution and then the mixed solution was electrophoresed with 15% acrylamide gel. The result is shown in the second lane from the left of FIG. 6. Further, 10 μl of the above CR aqueous solution was mixed with 2 μl of a 50 μM Cho-siRNA aqueous solution and then electrophoresed in a similar manner. The result is shown in the far right lane of FIG. 6. Further, as a control, the result of similarly electrophoresed siRNA alone is shown in the far left lane and the second lane from the right.

As is clear from FIG. 6, in all cases of siRNA alone, it is migrated towards the downstream, while the mixtures with CR became unmigrated in both cases of tocopherol-bound and cholesterol-bound siRNAs. This is considered to be resulted from the binding of siRNA and CR which has a large diameter and has no electric charge and therefore resulted in no migration.

(2) Fluorescence Correlation Spectroscopic Experiment

Rat chylomicron prepared in the similar manner as in the above Example 10 (1) was mixed with fluorescently labeled cholesterol-bound siRNA or tocopherol-bound siRNA and then the diffusion time was measured by fluorescence correlation spectroscopy (FCS) with reference to a literature (Biochemistry 41; 697-705. 2002). The measurement results are shown in FIG. 7.

As is clear from FIG. 7, the diffusion time became nearly 30 times longer in the case of a complex added with chylomicron as compared to the case of siRNA alone. Since the diffusion time is proportional to the diameter of a measured substance, it is considered that the diameter of the substance comprising siRNA has become larger due to the binding with chylomicron. Supposing that the length of siRNA is in the vicinity of 6 nm, the diameter of the complex of a group added with chylomicron is approximately 180 nm (theoretical value). The diameter of chylomicron itself (FIG. 8) measured by dynamic light scattering (DLS) was almost consistent with this value.

Example 11

In Vivo siRNA Delivery by Toc-siRNA

To examine whether the Toc-siRNA conveys its siRNA in vivo, the following experiment was performed.

First, in accordance with the above method described in Example 3, a Toc-siRNA labeled with Cy3 fluorescence dye was administered to a mouse. After a lapse of 1 hour, the mouse was killed and the liver was taken out.

Next, a part of the liver was fixed in a 4%-by-mass paraformaldehyde/PBS solution for 6 hours, and immersed in a 30% sucrose/PBS solution overnight at 4° C. The fixed liver was embedded in OCT compound (Sakura Finetek Japan Co., Ltd.: Tokyo, Japan), frozen by liquid nitrogen, and then segmented to 4 micro-m thickness with Leica CM3050 Cryostat (Leica: Germany). The frozen segment was moved onto Super Frost plus Microscope glass slide (Fisher Scientific: Pittsburgh, Pa., U.S.A), counterstained for 20 minutes using 13 nM Alexa-488 Phalloidin (Invitrogen)/PBS solution and 40 nM Topro-3 (Invitrogen)/PBS solution. Then the segment was enclosed in a vector shield (Vector: Burlingame, Calif., U.S.A) and observed with LSM 510 confocal scanning microscopy (Zeiss: Germany) (FIG. 9A).

FIG. 9A is an observation of the neighboring area of the liver sinusoid. The Cy3 fluorescence-dye signals were generally detected intensely on the part surrounding the blood vessel (the right part of the image divided by the dashed line in FIG. 9A), and it was confirmed that siRNAs were introduced into the hepatic cells (by way of example, the cells shown by triangles in FIG. 9A) and nonparenchymal cells (by way of example, the cells shown by arrows in FIG. 9A). This demonstrates that a Toc-siRNA is capable of conveying its siRNA to the liver.

Example 12

Efficient Toc-siRNA Processing In Vivo

To examine whether a Toc-siRNA taken into a hepatic cell is processed into a matured form of siRNA, the following experiment was performed.

First, in the same manner as in the above method described in Example 3, the liver of a mouse 1 hour after a Toc-siRNA administration was provided, and the detection of siRNA was performed in accordance with the above method described in Example 5 (FIG. 9B). As can be seen from the result of FIG. 9B, a processed 21-mer siRNA was confirmed to exist in addition to the original 27/29-mer siRNA. This shows that the Toc-siRNA was taken into a hepatic cell and then cleaved from the 27/29-mer siRNA into the 21-mer siRNA by a dicer existing in the cytoplasm.

Example 13

Animal Testing Related to Gene-Silencing by Toc-siRNA

To examine the ability of a Toc-siRNA to reduce a target gene expression in vivo, the following experiment was performed.

First, in the same manner as in the above method described in Example 3, the mouse was administered with the TocsiRNA, killed after a lapse of 24 hours, and the liver was taken out. Next, in accordance with the above-method described in Example 4, a quantitative RT-PCR was performed, and mRNA expressions were measured for each of the apoB gene, GAPDH gene, and TTR gene. The results are shown in FIG. 10A. As can be seen from FIG. 10A, in the case of a Toc-siRNA using an siRNA targeted to the mouse apoB gene (apoB-1 Toc-siRNA), the apoB mRNA expression was significantly reduced (n=3, P<0.001) as compared to the case of a Toc-siRNA using an siRNA unrelated to the apoB (control Toc-siRNA) or the case of a solvent only (maltose). Further, the relative mRNA expressions (relative expression based on the total RNA) of other endogenous genes (GAPDH gene, TTR gene) expressed on the liver were in the same range as compared to the case of administering the control Toc-siRNA or maltose only. The above fact demonstrates that the Toc-siRNA (apoB-1 Toc-siRNA) specifically reduces only the target gene expression in the liver and that it does not affect non-specific gene expressions, i.e., that the Toc-siRNA does not have an off-target effect.

Next, the timings of the samplings from the Toc-siRNA-administered mice were staggered and the time-dependent change was measured. The results are shown in FIG. 10B. As can be seen from FIG. 10B, the continuity of the apoB-gene expression-suppressing activity by the apoB-1 Toc-siRNA was observed until 2 days after the Toc-siRNA administration, while by day 4, the expression returned to the same level as others (control Toc-siRNA, maltose).

Further, a similar experiment was performed by gradually changing the dose of Toc-siRNA. The results are shown in FIG. 10C. The apoB-1 Toc-siRNA's expression-suppressing activity for the apoB gene was dose dependent. The dose of 32.0 mg/kg resulted in an activity of at least 80% expression suppression.

Example 14

Confirmation Test for Toc-siRNA-Related Side Effects

In accordance with the above method described in Example 3, the Toc-siRNA-administered mice were examined for side effects.

Specifically, blood was collected from the mice 3 days after the administration of 2 mg/kg Toc-siRNA/LP, measured for the white blood cell count (WBC), blood platelet count (Plt) in the blood and was biochemically analyzed on the total amount of protein (TP), aminotransaminase (AST, ALT) and blood urea nitrogen level (BUN).

Further, the interferon (IFN) induction was examined in the mice 3 hours after the administration of 2 mg/kg Toc-siRNA/LP. First, an ELISA kit with the detection limit of 12.5 pg/ml (PBL Biochemical Laboratories, Biosource) was used to measure the interferon-alpha (IFN alpha) concentration in the serum, but no IFN alpha was detected. Additionally, an attempt was made with an RT-PCR to confirm the expression of interferon-beta in the liver of the mice administered with 2 mg/kg of Toc-siRNA, but none was detected.

The results of the above experiments are shown in Table 1. The above facts show that the Toc-siRNA causes almost no side effects, and that the gene suppression by the Toc-siRNA is not caused by an interferon response.

| Treatment | | IFN-α (pg/ml) | BUN (mg/dl) | TP (g/dl) | AST (U/l) | ALT (U/l) | WBC (/μl) | Plt (×10$^4$/μl) |
|---|---|---|---|---|---|---|---|---|
| IFN-α, BUN, TP, AST, ALT, WBC and Plt levels in mouse serum after intravenous injection of Toc-siRNA or maltose. * | | | | | | | | |
| apoB1 Toc-siRNA | 3 h | <12.5 | | | | | | |
| | 24 h | | 19.1 ± 1.0 | 5.1 ± 0.1 | 78 ± 1 | 21 ± 3 | 2800 ± 330 | 122.0 ± 0.3 |
| | 48 h | | 24.0 ± 2.4 | 5.5 ± 0.1 | 67 ± 4 | 22 ± 1 | 2600 ± 550 | 112.2 ± 18.9 |
| maltose | 3 h | <12.5 | | | | | | |
| | 24 h | | 22.0 ± 0.9 | 5.5 ± 0.1 | 79 ± 9 | 25 ± 2 | 2600 ± 560 | 117.9 ± 13.8 |
| | 48 h | | 24.5 ± 1.5 | 5.5 ± 0.1 | 60 ± 3 | 26 ± 3 | 3700 ± 900 | 109.0 ± 7.0 |

* Values represent mean ± S.E. (n = 3)

Example 15

Preparation of an Alpha Tocopherol-Bound-siRNA- or Cholesterol-Bound-siRNA-Containing Lipoprotein A lipoprotein-rich serum with high chylomicron content provided in accordance with the above method described in Example 2 was adjusted with 10%-by-mass maltose solution to obtain a triglyceride concentration of 20 g/L. Toc-siRNA (1 micro-g/micro-1, in terms of the amount of siRNA) was mixed with the same volume of the lipoprotein-rich serum (20 g/L triglyceride concentration). The mixture was incubated at 37° C. for 1 hour, and an alpha-tocopherol-bound-siRNA-containing lipoprotein was obtained (hereinafter also referred to as "Toc-siRNA/LP"). Further, cholesterol-bound-siRNA-containing lipoprotein (hereinafter, also referred to as "Cho-siRNA/LP") was obtained in the similar manner except for using Cho-siRNA in place of Toc-siRNA.

Example 16

Efficient Toc-siRNA/LP Processing In Vitro

To examine whether a Toc-siRNA/LP taken into a cell is processed into a matured form of siRNA, the following experiment was performed.

First, a Hepa 1-6 cell line having been cultured in a medium without a transfection reagent was added with 100 nM Toc-siRNA/LP and then further cultured for 6 hours.

Using this Hepa 1-6 cell line, a northern blot analysis was performed in accordance with the above method described in Example 5. The result is shown in FIG. 11. As can be seen from FIG. 11, a processed 21-mer siRNA was confirmed to exist in addition to the original 27/29-mer siRNA. This shows that a Toc-siRNA/LP can be taken into a cell of the Hepa 1-6 cell line and that the 27/29-mer siRNA was cleaved into a 21-mer siRNA by a dicer existing in the cytoplasm.

Example 17

Animal Testing Related to siRNA Delivery and Gene-Silencing by Toc-siRNA/LP

To examine the Toc-siRNA/LP's ability to deliver its siRNA in vivo or the ability to reduce a target gene expression in vivo, the following experiment was performed.

First, in accordance with the above method described in Example 3, a mouse was administered with a Toc-siRNA/LP and killed after a lapse of 2 days and the liver was taken out. Using this liver, a quantitative RT-PCR was performed in accordance with the above method described in Example 4, and mRNA expressions were measured for each of the apoB gene, GAPDH gene, and TTR gene. The results are shown in FIG. 12. As can be seen from FIG. 12A, in the case of a Toc-siRNA/LP using an siRNA targeted to the mouse apoB gene (ApoB Toc-siRNA/LP vector), the apoB mRNA expression was significantly reduced (n=3, P<0.001) as compared to the case of a Toc-siRNA/LP using an siRNA unrelated to the apoB (Unrelated siRNA/LP) or the case of LP only (control (LP only)). Further, the results of FIG. 12B show that this expression-reduction effect is apoB-gene specific. More specifically, even when a Toc-siRNA/LP using an siRNA targeted to the apoB gene was administered, the relative mRNA expressions (relative expression based on the total RNA) of other endogenous genes (GAPDH gene, TTR gene) expressed on the liver were in the same range as compared to the case of administering LP only.

Subsequently, the same experiment was performed by gradually changing the dose of Toc-siRNA/LP. The results are shown in FIG. 12C. The Toc-siRNA/LP's expression-suppressing activity (knockdown effect) for the apoB gene was dose dependent. Even the dose of 1.0 mg/kg resulted in an activity of at least 80% expression suppression.

Further, to examine the effect of feeding after fasting (administration of protein-rich fluid food) on the expression-suppressing effect of Toc-siRNA/LP, an expression-suppressing activity was measured in a case where the protein-rich fluid food was not administered in the above experiment. The results are shown in FIG. 13. As can be seen from FIG. 13, the expression-suppressing activity was reduced by 31% in the case without feeding (Feeding (−)) as compared to the case with feeding (Feeding (+)). This suggests that a Toc-siRNA/LP is taken in via an LRP-1 receptor expressed on the liver, which receptor is activated by feeding to take in chylomicron remnants.

Example 18

SiRNA Delivery with Toc-siRNA/LP or Cho-siRNA/LP by Intraperitoneal Administration to Rat Fluorescently-labeled Toc-siRNA/LP or Cho-siRNA/LP was prepared in accordance with the description of the above Example 15 by labeling siRNAs with Cy3 fluorescent dye, which was then administered intraperitoneally at 8 mg/kg in terms of the nucleic acid amount to 3 week-old SD rats (Charles River Japan: Kanagawa, Japan). 8 hours after, the liver segments were observed under a confocal microscope, and the results are shown in FIG. 14. The fluorescent dye was found to exist in almost all hepatic cells in both cases of Toc-siRNA/LP or Cho-siRNA/LP administration. No significant difference was observed between the two cases.

Example 19

Confirmation Test for Toc-siRNA/LP-Related Side Effects

As with the above Example 14, a biochemical analysis and the like were performed also on the blood of a mouse administered with Toc-siRNA/LP (Table 2).

In addition, the liver was taken out from the Toc-siRNA/LP-administered mouse in the above method described in Example 3. A part of the liver was fixed in 4%-by-mass paraformaldehyde, embedded in paraffin, and a 4 micro-m-thick segment was produced. The segment was subjected to a hematoxylin-eosin staining for a pathologic analysis. Further, as a control, results of a hematoxylin-eosin staining are shown for the liver segment of a mouse administered with LP only in place of Toc-siRNA/LP (FIG. 15).

As stated above, no particular abnormality was observed in both the biochemical analysis of the blood and pathological analysis of the liver tissues of the Toc-siRNA/LP-administered mouse.

Further, as with the above Example 14, the interferon induction was examined in the Toc-siRNA/LP-administered mouse, but none was detected.

The above facts show that, as with the above Toc-siRNA, a Toc-siRNA/LP causes almost no side effects.

TABLE 2

| | [Biochemical analysis and cell count of the blood] Biochemical analysis and cell count of the blood | | | | | | |
|---|---|---|---|---|---|---|---|
| | TP (g/dl) | Alb (g/dl) | T-Bil (mg/dl) | BUN (mg/dl) | Cre (mg/dl) | Na (mEq/l) | K (mEq/l) |
| Toc-siRNA/LP | 5.3 ± 0.2 | 3.4 ± 0.2 | 0.05 ± 0.01 | 28.4 ± 1.5 | 0.14 ± 0.02 | 151 ± 4 | 5.5 ± 0.3 |
| LP only | 5.1 ± 0.1 | 3.4 ± 0.1 | 0.05 ± 0.01 | 22.7 ± 2.3 | 0.13 ± 0.01 | 151 ± 1 | 4.7 ± 0.4 |
| | AST (U/l) | ALT (U/l) | LDH (U/l) | Alp (U/l) | RBC ($\times 10^4/\mu l$) | WBC (/$\mu l$) | Plt ($\times 10^4/\mu l$) |
| Toc-siRNA/LP | 57 ± 5 | 21 ± 1 | 278 ± 6 | 541 ± 58 | 791 ± 22 | 6300 ± 600 | 122 ± 3 |
| LP only | 48 ± 2 | 17 ± 1 | 258 ± 27 | 467 ± 53 | 816 ± 13 | 6600 ± 200 | 92 ± 13 |

Example 20

Comparisons with Other Non-Viral Vectors

In vivo efficiency of apoB mRNA-expression suppression in a mouse liver was compared between other already reported non-viral vectors (Nature 432:173-178, 2004; Nature 441; 111-114, 2006; ACS Chem Biol 2; 237-241, 2007; Proc Natl Acad Sci USA 104; 12982-12987, 2007; Nature Biotechnology 25:1149-1157, 2007). The results are shown in FIG. 16. The siRNAs used in other known viral vectors are same as the siRNA used in the Toc-siRNA or Toc-siRNA/LP of the present invention, and are targeted to the same region of the mouse apoB mRNA (Nature 432:173-178, 2004). Further, as the data for the Toc-siRNA of the present invention, the value of apoB-1 Toc-siRNA (1 day after the administration of 2.0 mg/kg) in the above FIG. 10B of Example 13 are used, and as the data for the Toc-siRNA/LP of the present invention, the value of Toc-si RNA/LP (2 days after the administration of 1.0 mg/kg) in the above FIG. 12C of Example 17 were used.

The results of FIG. 16 show that the present invention, in particular the Toc-siRNA/LP, is highly superior as compared to other siRNA delivery systems, in terms of the required amount of siRNA and its expression-suppressing activity.

INDUSTRIAL APPLICABILITY

According to the method of delivering nucleic acids of the present invention, nucleic acids such as an siRNA for suppressing a target gene expression can be delivered in vivo more safely and efficiently. According to the expression-suppressing agent and pharmaceutical composition utilizing the delivery method of the present invention, the expression of a specific gene that causes a disease can be suppressed in vivo more safely and efficiently. Further, according to the treatment method of the present invention utilizing the delivery method of the present invention, the expression of a specific gene that causes a disease can be suppressed in vivo more safely and efficiently and consequently, the disease can be treated more safely and efficiently.

The invention claimed is:

1. A complex comprising:
   a. nucleic acids for suppressing a target gene expression, wherein the nucleic acids are bound to vitamin E; and
   b. a chylomicron.

2. The complex according claim 1, wherein the nucleic acids are one or more kinds of nucleic acids selected from the group consisting of siRNA, shRNA, antisense oligonucleotide, antagomir, nucleic-acid aptarner, ribozyme, and decoy.

3. The complex according to claim 2, wherein the nucleic acids are siRNA.

4. The complex according to claim 3, wherein the nucleic acids are RNA subjected to an anti-RNase treatment.

5. The complex according to claim 4, wherein the anti-RNase treatment is 2'-O-methylation treatment and/or thiophosphorylation treatment.

6. A method for in vivo delivering nucleic acids for suppressing a target gene expression, comprising the following step (C):
   (C) binding vitamin E and the nucleic acids and administering the same to a vertebrate, wherein a production of endogenous chylomicron or chylomicron remnant is induced in the vertebrate.

7. The method according to claim 6, wherein the step (C) comprises binding vitamin E and the nucleic, acids and administering the same to a vertebrate within 12 hours after the vertebrate is administered with a lipid.

8. The method according to claim 7, wherein the lipid is orally administered.

9. The method according to claim 6, further comprising the following step (A') before step (C):
   (A') administering triton to a vertebrate before a production of endogenous chylomicron or chylomicron remnant is induced in the vertebrate.

10. The method according to claim 6, further comprising the following step (B) before step (C):
    (B) administering LPL and/or heparin to a vertebrate before administering the nucleic acids to the vertebrate.

11. The method according to claim 6, further comprising, the following step (A) before step (C):

---

SEQUENCE LISTING

```
<160> NUMBER OF SEQ ID NOS: 2

<210> SEQ ID NO 1
<211> LENGTH: 27
<212> TYPE: RNA
<213> ORGANISM: Artificial
<220> FEATURE:
<223> OTHER INFORMATION: siRNA sense strand

<400> SEQUENCE: 1
gucaucacac ugaauaccaa ugcugga                                       27

<210> SEQ ID NO 2
<211> LENGTH: 29
<212> TYPE: RNA
<213> ORGANISM: Artificial
<220> FEATURE:
<223> OTHER INFORMATION: siRNA antisense strand

<400> SEQUENCE: 2
uccagcauug guauucagug ugaugacac                                     29
```

(A) allowing a vertebrate to be in a state of starvation prior to the administration of a lipid.

12. The method according to claim 6, wherein step (C) comprises administering to a vertebrate the nucleic acids bound to vitamin E after mixing the same with concentrated chylomicron obtained from the vertebrate.

13. The method according to claim 12, further comprising the following step (B) before step (C):

(B) administering LPL, and/or heparin to a vertebrate before administering the nucleic acids to the vertebrate.

14. The method according to any one of claims 6 to 13, wherein the nucleic acids are one or more kinds of nucleic acids selected from the group consisting of siRNA, shRNA, antisense oligonucleotide, antagomir, nucleic-acid aptamer, ribozyme, and decoy.

15. The method according to claim 14, wherein the nucleic acids are siRNA.

16. The method according to claim 15, wherein the nucleic acids are RNA subjected to an anti-RNase treatment.

* * * * *

UNITED STATES PATENT AND TRADEMARK OFFICE
CERTIFICATE OF CORRECTION

PATENT NO. : 8,329,670 B2
APPLICATION NO. : 12/787552
DATED : December 11, 2012
INVENTOR(S) : Takanori Yokota et al.

Page 1 of 1

It is certified that error appears in the above-identified patent and that said Letters Patent is hereby corrected as shown below:

Column 24, claim 1, line 4, the term "hound" should read --bound--.

Column 24, claim 2, line 6, the term "according claim 1" should read --according to claim 1--.

Column 24, claim 2, line 9, the term "aptarner" should read --aptamer--.

Column 24, claim 7, line 26, the term "nucleic, acids" should read --nucleic acids--.

Column 24, claim 11, line 40, the term "further comprising," should read --further comprising--.

Signed and Sealed this
Twelfth Day of March, 2013

Teresa Stanek Rea
*Acting Director of the United States Patent and Trademark Office*